United States Patent [19]

Peoples et al.

[11] Patent Number: 5,661,026

[45] Date of Patent: Aug. 26, 1997

[54] GENE ENCODING BACTERIAL BETA-KETOTHIOLASE

[75] Inventors: Oliver P. Peoples, Arlington; Anthony J. Sinskey, Boston, both of Mass.

[73] Assignee: Massachusetts Institute of Technology, Cambridge, Mass.

[21] Appl. No.: 435,083

[22] Filed: May 4, 1995

Related U.S. Application Data

[62] Division of Ser. No. 297,667, Aug. 29, 1994, Pat. No. 5,512,669, which is a continuation of Ser. No. 124,570, Sep. 20, 1993, abandoned, which is a continuation of Ser. No. 944,488, Nov. 3, 1992, abandoned, which is a division of Ser. No. 566,535, Aug. 13, 1990, Pat. No. 5,229,279, which is a continuation of Ser. No. 67,695, Jun. 29, 1987, abandoned.

[51] Int. Cl.$^6$ .......................... C12N 15/54; C12N 15/74; C12N 15/75

[52] U.S. Cl. ................ 435/252.3; 435/252.71; 435/193; 536/23.2

[58] Field of Search .................. 435/193, 252.3, 435/252.31; 536/23.2

[56] References Cited

U.S. PATENT DOCUMENTS 4,477,654  10/1984  Holmes et al. ............... 528/361

OTHER PUBLICATIONS

Peoples, O. P., et al. (1987) J. Biol. Chem. 262 (1), 97–102.
D. F. Berg and C. M. Berg, "The Prokaryotic Transposable Element TN5," *Bio/Technology*, 1:417–435 (1983).
G. Ditta, et al., "Broad host range DNA clonig system for Gram–negative bacteria: Construction of a gene bank of Rhizobium meliloti," *Proc. Natl. Acad. Sci. USA*, 77:(12)7347–7351 (1980).
Klechner N. et al., "Genetic Engineering in Vivio Using Translocatable Drug–resistance Elements," *J. Mol. Biol.*, 116:125–159 (1977).
Peoples, O.P., "Biosynthetic Thiolase from Zoogloea ramigera," *J. Biol. Chem.*, 262:(1)97–102 (1987).
Slater, et al., "Cloning and Expression in Escherichia coli of the Alcaligenes eutrophus H16 Poly–β–Hydroxybutyrate Biosynthetic Pathway," *J. Bacteriol*, 170:(10)4431–4436 (1988).
Simon, R. et al., "A Broad Host Range Mobilization System For In Vivo Genetic Engineering: Transposon Mutagenesis In Gram Negative Bacteria," *Bio/Technology*, 1:(9) 784–791 (1983).
Simon, R. et al., "High frequency mobilization of gram–negative bacterial replicons by the in vitro constructed Tn5–Mob transposon," *Mol. Gen. Genet*, 196:413–420 (1984).

Spratt S.K., et al., "Cloning, Mapping, and Expression of Genes Involved in the Fatty Acid–Degradative Multienzyme Complex of *Escherichia coli*," *J. Bacteriology*, 158:(2) 535–547 (1984).
Suggs, S.V., et al., "Use of synthetic oligonucleotides as hybridization probes: Isolation of cloned cDNA sequences for human β–microglobulin," *Proc. Natl. Acad. Sci. USA*, 78:(11) 6613–6617 (1981).
Young, R.A. and Davis, R.W., "Efficient isolation of genes by using antibody probes," *Proc. Natl. Acad. Sci. USA* 80:1194–1198 (1983).
Young, R.A. and Davis, R.W., "Yeast RNA Polymerase II Genes; Isolation with Anitbody Probes," *Science*, 222:778–782 (1983).
Senior and Dawes, *Biochemical Journal*, 134, 224–238 (1973).
Oeding and Schlegel, *Biochemical Journal*, 134, 239–248 (1973).
Berndt and Schlegel, *Arch. of Microbiol.*, 103, 21–30 (1975).
Nishimura, et al., *Arch. Microbiol.*, 116, 21–27, (1978).
Saito, et al., *Arch. Microbiol.*, 114, 211–217 (1977).
Fukui, et al., *Biochem. Biophys. Acta.*, 917, 365–371, (1987).
Fukui, et al., *Arch. Microbiol.*, 110, 149–156, (1976).
deSmet, et al., *Journal of Bacteriology*, 154(2), 870–878 (1983).
Schlegel, et al., *Arch. Microbiol.*, 71, 283–294 (1970).

*Primary Examiner*—Charles L. Patterson, Jr.
*Attorney, Agent, or Firm*—Arnall Golden & Gregory

[57] ABSTRACT

The present invention is a method for controlling biopolymer synthesis by determining the genetics and enzymology of polyhydroxybutyrate (PHB) biosynthesis at the molecular level. The purified enzymes and genes provide the means for developing new PHB-like biopolymers having polyester backbones. Specific aims are to 1) control the chain length of the polymers produced in fermentation processes through genetic manipulation, 2) incorporate different monomers into the polymers to produce co-polymers with different physical properties, and 3) examine the physical/rheological properties of these new biopolymers in order to develop further design criteria at the molecular level.

The method for engineering biopolymer synthesis includes: isolation and characterization of the genes for the enzymes in the synthetic pathway (beta-ketothiolase, acetoacetyl-CoA reductase and PHB synthetase); cloning of the genes in a vector(s); placement of the vector(s) under the control of regulated promoters; expression of the genes; determination of the function and use of other factors such as substrate specificity in polymer production and composition; and isolation and physical and chemical analysis of the resulting polymers.

5 Claims, 13 Drawing Sheets

FIGURE 3a

```
-210              -190                -170                  -150              -130                 -110
ACAATCGAAT TCTGCGATGC GGGGAGGAT GCTGCGCAAC ATGGATTTTC ATGCTGCGGG GCCCCCGCA TGAAATTTTA GGGCCGGCGG CCTCTTTTCT TTTTGAGCC TTGCGAGTAT CCGCAAAAAG ACGCTTCCTG
                                                 EcoR1                                                                                            "-35"
                                                 GAATTCCTCA TCCCCGTGTT                                                                            ATATCCCGTT TGACTCTCCT
                                                                -90 RNA →                                                                               -10
TCTCCGCTTT GCCAGTTTTG ATTTCGGGAC AACCCGCGGG CTCGCGCCGT TCGTGCCGCC GACCCGGTTC CAAGGCCGGC CGGAAGGCTG CCAGAACTGA GGAAGCACAT
        "-10"                                                                                                            SD                90
            10               30              50               70
ATG AGC ACC CCG TCC ATC ATC GTC ATC GCC AGC GCC GTC GGT TCC TTC AAC GGC GCT TTC GCC AAC ACG CCC GCC CAT GAA CTC
Met Ser Thr Pro Ser Ile Val Ile Ala Ser Ala Arg Thr Ala Val Gly Ser Phe Asn Gly Ala Phe Ala Asn Thr Pro Ala His Glu Leu
                110                         130                         150                         170
GGG GCG ACC GTG ATT TCG GCG CTT CTC GAG CGC GGC GTT GCG GCG GCA GGC GAG GTG AAC GAG GTG ATT CTC GGC GTG CTG CCG GCC
Gly Ala Thr Val Ile Ser Ala Leu Leu Glu Arg Gly Val Ala Ala Gly Glu Val Asn Glu Val Ile Leu Gly Val Leu Pro Ala
        190                         210                         230                         250                         270
GCC GAA GGC CAG AAC CCG CAG GCC CCG CAG CCG CCG CAG GCG CCG CAG ATC GCC ACG GCC GAT GCG AGC ATC ATC GTC GCC GGC GCC
Ala Glu Gly Gln Asn Pro Gln Ala Pro Gln Arg Gln Ala Met Lys Ala Gly Val Pro Gln Ala Thr Gly Ala Ser Ile Ile Val Ala Gly Gly
        290                         310                         330                         350
TCG GGC CTG CGG GCC GTC GCG CTC GGC ATG CAG CAG ATC GCC ACG GCC GAT GCG AGC ATC ATC GTC GCC GGC ATG GAA TCC ATG TCC
Ser Gly Leu Arg Ala Val Ala Leu Gly Met Gln Gln Ile Ala Thr Gly Asp Ala Ser Ile Ile Val Ala Gly Met Glu Ser Met Ser
        370                         390                         410                         430                         450
ATG GCC CCG CAT TGC GCG CAT CTG GCC GGC GTG AAG ATG GGC GAT TTC AAG ATG GGC GAT TTC AAG ATG ATC GAC ACG GCC CTG ACC GAC GCC
Met Ala Pro His Cys Ala His Leu Ala Gly Val Lys Met Gly Asp Phe Lys Met Gly Asp Phe Lys Met Ile Asp Thr Gly Leu Thr Asp Ala
        470                         490                                510                         530
TTC TAC GGC TAC CAC ATG GGC ATG ACC GCC AAG CAG TGG CAG CTT TCC CGC GAC GAG CAG GAC GCC TTC GCC GTC GCC
Phe Tyr Gly Tyr His Met Gly Met Thr Ala Lys Gln Trp Gln Leu Ser Arg Asp Glu Gln Asp Ala Phe Ala Val Ala
```

```
                550                    570                    590                    610                               630
TCG CAG AAC AAG GCC GCC CAG AAG GAC GGC TTC CGC AAG GAC GAG ATC GTC CCC TTC ATC GTC AAG GGC CGC AAG GGC GAC ATC
Ser Gln Asn Lys Ala Ala Gln Lys Asp Gly Phe Arg Lys Asp Glu Ile Val Pro Phe Ile Val Lys Gly Arg Lys Gly Asp Ile
                                            650                    670                    690                    710

ACG GTC GAT GCC GAC GAA TAT ATC CGC CAC CGC GGC ACG CTC GAT TCC ATG GCG AAG CTC CGG GCC TTC GAC AAG GAA GGC GTG
Thr Val Asp Ala Asp Glu Tyr Ile Arg His Arg Gly Thr Leu Asp Ser Met Ala Lys Leu Arg Pro Ala Phe Asp Lys Glu Gly Val
                                            730                    750                    770                    790                810

ACG CCC AAC GCC TCC CGC CTC AAT GAC GGC CTC AAT GAC AAT GCC GGC GCC GCC GCC CTG ATG AGC GAA GCC TCG CGC CGC ATC CAG CCG
Thr Ala Gly Asn Ala Ser Gly Leu Asn Asp Ala Ala Ala Leu Met Ser Glu Ala Ser Arg Arg Gly Ile Gln Pro
                    830                    850                    870                    890

CTC GGC CGC ATC GTT TCC TGG GCG ACG GTC GAT CCC AGG GTC ATG GGC ACC GCC CCG ATC CCG GCC TCC AAG CGG CTC GAG
Leu Gly Arg Ile Val Ser Trp Ala Thr Val Asp Pro Lys Val Met Gly Thr Ala Pro Ile Pro Ala Ser Arg Lys Ala Leu Glu
            910                    930                    950                    970                    990

CGC GGC AAG ATC GGC GAT CTC GAC CTC GTG GAA GCC AAC GAA GCC TTC GCG CAG GCC TGC GTC GTC AAC AAG GAC CTC GGA
Arg Ala Gly Trp Lys Ile Gly Asp Leu Asp Leu Val Glu Ala Asn Glu Ala Phe Ala Gln Ala Cys Ala Val Asn Lys Asp Leu Gly
            1010                   1030                   1050                                          1070

TGG GAT CCG TCC ATC GTC AAC GTC AAC GGT GCC AAC GGT ATC ATC GGT CAC CCG ATC GGG TCC GCG GCC ATC CTC AAC ACG CTC
Trp Asp Pro Ser Ile Val Asn Val Asn Gly Ala Asn Gly Ile Ile Gly His Pro Ile Gly Ala Ser Gly Ala Arg Ile Leu Asn Thr Leu
                    1090                   1110                   1130                   1150                   1170

CTC TTC GAG ATG AAG CGT CGC GGC GGC CGC AAG GGT CTC GCC ACG CTC TGC GGG GCG GTG GCG ATG TGC ATC GAG AGC
Leu Phe Glu Met Lys Arg Arg Gly Gly Arg Lys Gly Leu Ala Thr Leu Cys Gly Ala Val Ala Met Cys Ile Glu Ser
                    1190                   1210                   1230

CTT TAG GCG TCA GCT TAT CCA AAA CTT TGC CAT GAC CTG CCG CCG AGG GCG ACA GGT CGA C
Leu End                                                                    SalI
```

FIGURE 3b

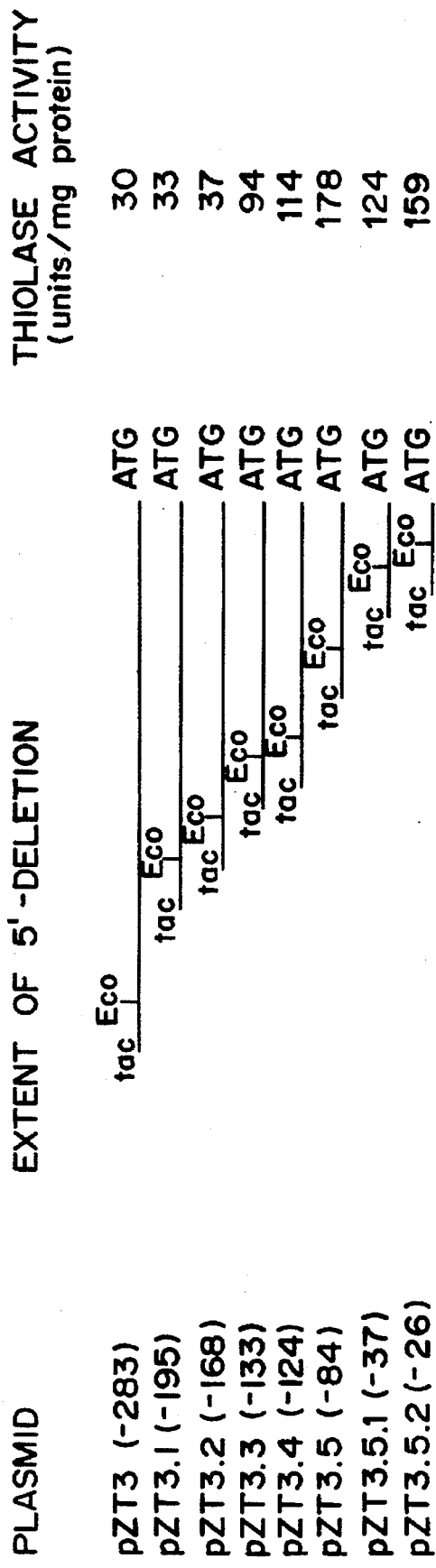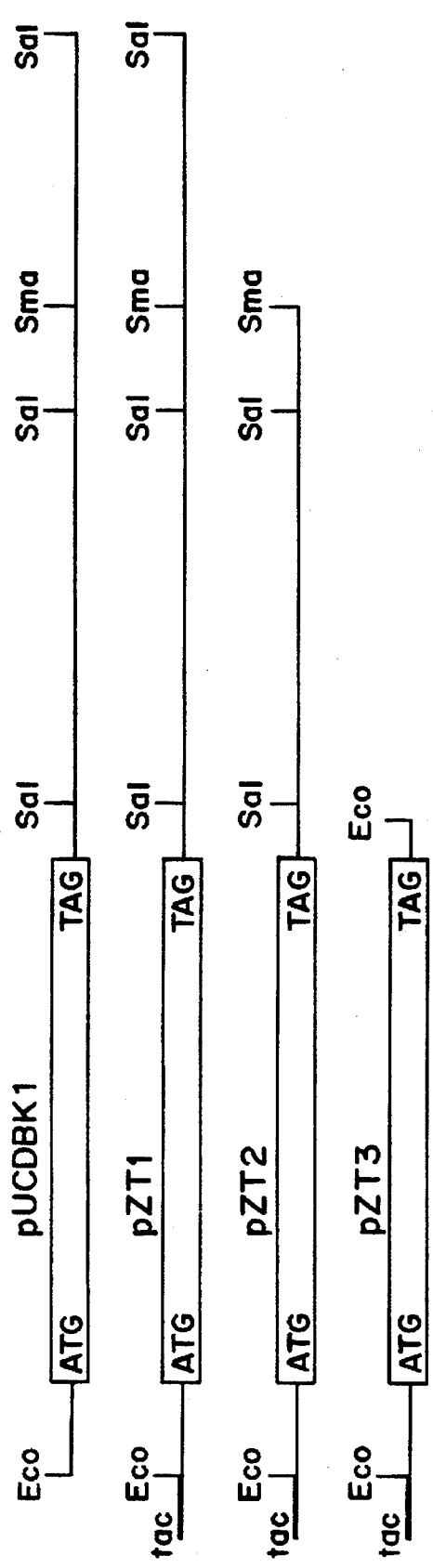

FIGURE 6a

```
     Sal
  1  GTCGACTCAAAAATCAGTCTAGGGAGTGAGCGACATGAGCAGGGTAGCATTGGTAACGGGGGATCCGGGGGCATCGCGGCAGCCATTTCGATT     96
                                MetSerArgValAlaLeuValThrGlyGlySerArgGlyIleGlyAlaAlaIleSerIle

97  GGGCTGAAGGCGGGGGATACAAGGTGGCTGCCAGCTATGCCGGCAATGACGATGCGGCAAGCCCTTCAAGGCGGAAACGGGCATCGCCCTCTAC    192
     AlaLeuLysAlaAlaAlaGlyTyrLysValAlaAlaSerTyrAlaAlaGlyAsnAspAspAlaAlaLysProPheLysAlaGluThrGlyIleAlaValTyr

193  AAGTGGGACGTGTCGAGCTACGAGGCCTGCGTTCGAGGGATCGCCAAGTGGAGGCCGATCTCGGCCGATTGACGTTCTCGTCAACAATGCGGGC    288
     LysTrpAspValSerSerTyrGluAlaCysValGlyGlyIleAlaLysValGluAlaAspLeuGlyProIleAspValLeuValAsnAsnAlaGly

289  ATCACCAAGGACGCGATGTTCCACAAGATGACGCCCGACAGTGAATGCGGTCATCAACACCAACCTCACGGTTCTCTTCAACATGACCCATCCG    384
     IleThrLysAspAlaMetPheHisLysMetThrProAspSerGluCysGlyHisGlnTrpAsnAlaValIleAsnThrAsnLeuThrValLeuPheAsnMetThrHisPro

385  GTCTGCTCCGGCATGCGGGACCTGCAGCTTCGGCGACCGCAGATGGTCAGGCGAACTATTCC    480
     ValTrpSerGlyMetArgAspArgSerPheGlyArgIleValAsnIleSerSerIleAsnGlyIleValGlnLysGlyIleMetGlyGlnAlaAsnTyrSer

481  GCCGCCAAGGCCCCGGACCTCGGCTTCACCAAGGGCTTGGCCAGGAAGGGCCATCAAGGGCATCGCTGGTTAGTACGGCCATCTGCCCGGCTATATC    576
     AlaAlaLysAlaProAspLeuGlyPheThrLysAlaLeuAlaLeuAlaGlnGluGlyIleArgLysIleThrValAsnAlaIleCysProGlyTyrIle

577  GGTACGGAAATGTGCGCGCCATTCCGAAAAGTGCTGAACGAGCGGATCATCCCGAAGCGGATCATCCCGCAGATCCCGGTCGGGAGCCGGAGATC    672
     GlyThrGluMetValArgAlaIleIleProGluLysValLeuAsnGluArgIleIleProGlnIleIleProValGlyArgLeuGlyArgLeuGlyGluProAspGluIle

673  GCCCGCATCGTCGTCTTCCTCGCCTTCGGACGAGGCCGGCCTTCATCACCGGCTTCGACGCTCGACATCTCGGCGAACTCGACCAGTTCTTCGTCTGATACCGG    768
     AlaArgIleValValPheLeuAlaSerAspGluAlaGlyPheIleThrGlyPheIleThrGlySerThrIleSerAlaAsnGlyGlyGlnPhePheVal*
```

```
769  CCACACGAAACGGAACGCGGGCGCCTTCGGGCCGTTTCATGTGGTATGCTGGTCGAAAGGAGACCCGATGAAACAGAAAGCTGGATGAGG   864
865  CGGGCGATTGCCGAGGCGCTGGCATCCCTCGAAGGATGGATTCCGCTCGGCTGACGCGGCCATCCGAGAAGCGCTACACGTTCAAGAGCTTCCGCG   960
961  AGGGCGTTCGGCTTCATGACCGAGGGCGCTGGCGGGGAGAAATTCAACCACCATCCCGAGAAATGTTCAACGTTCTACAATCGGCTCGACGTGCGGC  1056
1057 TGACCAACCACGATGCGGGCCGGCTGACCGAGCTGACTTCAAGCTGGGCGGCGATGGAGAAGGCGGCCTTTCGCACCGAAGAGTTGAAGCCG     1152
1153 GCCTGAACGGCATTCCCATATGATCAGCCGCCCGACTGTGTCCGGGCTGCCCCGAGGGAGGCCTTGAATGACGATGTGAAGATCGGCGAGATTCT   1248
1249 GCTGCCCCGGCGACAAGGACGAGCAGGAGCGTCAGGAAAGCCGCTGAGCCGGTTCTCGGCCGGCTCTCAAGCCGCGATGGGCCAGGTTCCCTT    1344
1345 CGCCCGCGATCTCGTGCGCTCCTACTATTGCGCGCGGCCCCACACCCGCGATCCCGCTCGATCGGGCGGCTCGCCTATTTGT          1440
1441 GCTCCGCCTCGAGACGGGCCATACCGGCGATTTCTTCGGCCTTGTCGCTGCTGACGAGCTTGCCGTCGACGTTGCCGCCCTTCGGCGCTACGCCGATCCGGGCCA  1535
1537 TGTTCGCGACGACCATTACGCGCCCGCCGACCGGCTTGCGGACGAGCCGGACATGCAACCCTTCGTTGAGCCGCCAATCGGGTC          1632
1633 AAATTCTTGCCCTATTCCTGTGCCATTAGGCATCTCGACGGGTTCATCTCGACGGCCTTCACCAAATGGGACTGGGACGCGGCCCGTTTCACGAAAAGGCTGCG  1728
1729 GCGGACTTCGACACGGGTTTCGTCCCGGGTGCTGTTGACGGTTTGTTAACCTGAATTAAGTCAAATA              1824
1825 AATCAAATCGTCATCAAGCATGCCCGACACCCGGTGAAAGGCATCCGCCTTCGGCCGGCAATCACTGGCAAGACAACCGGCAGGAAAACATCTTC  1920
1921 GTAAGAAAGCTCGCAACTCGCCACTCGCCCCCTCGTCCTTGCCAGGGCCGTTGCCTGCGGCCAAACGCCGCATTCAGCAGTTCAATGCCTGG    2016
2017 GGGGCCCTATTCCTATCAGGCGAATGCGGCAAGGTCTGCTCGTCTCCGTGCCGAAGGAAAAGACGCCCCCGGG  2094
                                                                              Sma
```

*FIGURE 6b*

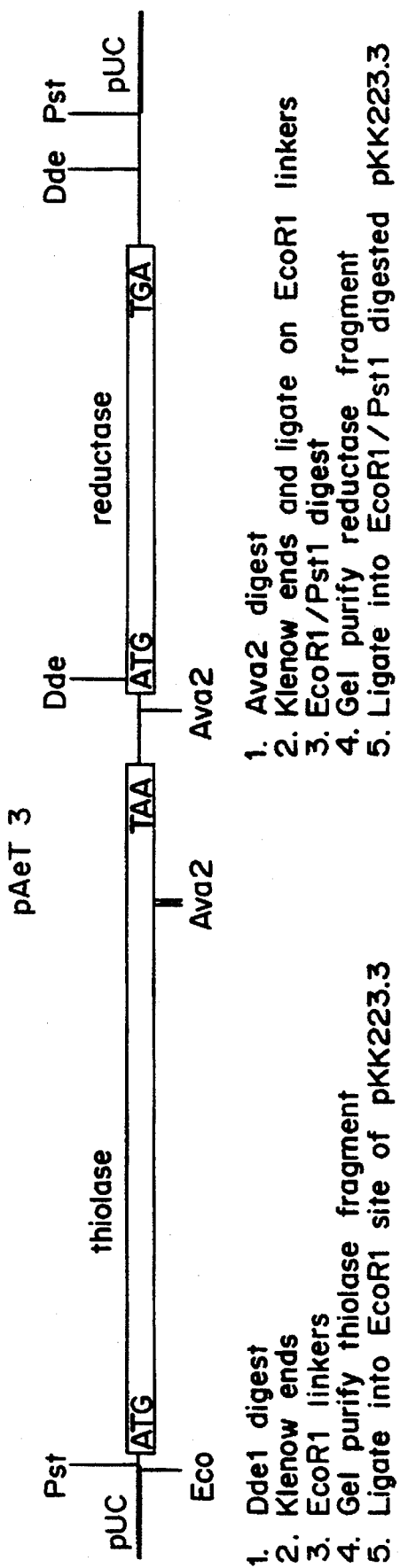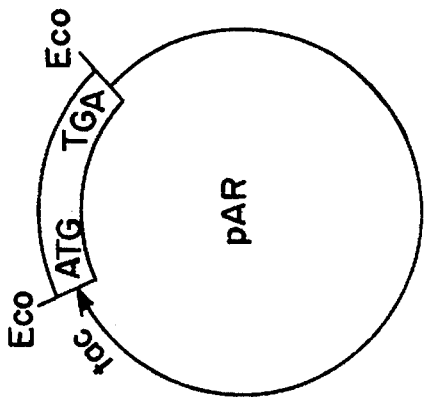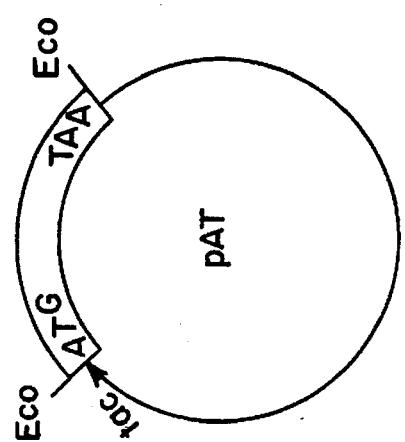
FIGURE 7

FIGURE 8a

```
        10              30              50              70              90
Pst     .               .               .               .               .
CTGCAGGTTCCCTCCCCGTTCCATTGAAAGGACTACACAATGACTGACGTTGTCATCGTATCCGCCGCCCGGTCGGCCAAGTTTGGCGGC
                                      MetThrAspValValIleValSerAlaAlaArgThrAlaValGlyLysPheGlyGly 110             130             150             170             190
        .               .               .               .               .
TCGCTGGCCAAGATCCCGGCACCGGAACTGGTCCTGTCATCAAGGCCGTGAGCCGGTCAAGCCGGAGCAGGTGAGCGAAGTC
SerLeuAlaLysIleProAlaProGluLeuGlyLeuValValIleLysAlaAlaLeuArgAlaGlyValLysProGluValSerGluVal 210             230             250             270
        .               .               .               .
ATCATGGGCCAGGTGCTGACCGCCGTTCGGCCAGAACCCCGGCCGATCAAGGCCCTGCCCGGCGATGTGCCGGCCATGACC
IleMetGlyGlnValLeuThrAlaLeuArgGlnAlaAsnProAlaArgGlnAlaAlaIleLysAlaLeuProAlaMetValProAlaMetThr 290             310             330             350             370
.               .               .               .               .
ATCAAACAAGGTGTGCGGCTCGGCCTGAAGGCCGTGCTGGCCAACGCGATCATGGCGGCCGACGCCGAGATCGTGGTGCCGGGCCAG
IleAsnLysValCysGlySerGlyLeuLysAlaValMetLeuAlaAlaAsnAlaIleMetAlaGlyAspAlaGluIleValValAlaGlyGlnGln 390             410             430             450             470
        .               .               .               .               .
GAAAACATGAGCGCCGCCCCACGTGCTGCCCGGCTCGCCCGGCGATGGTTCCGCAGGCCGATGGCCAAGCTGTCGACACCATGATCGTCGACGGC
GluAsnMetSerAlaAlaProHisValLeuProGlySerArgAspGlyPheArgMetGlyAspAlaLysLeuValAspThrMetIleValAspGly 490             510             530             550             570
        .               .               .               .               .
CTGTGGGACGTGTACAACCAGTACCACACCGGCATCACCCCGAGAATACGGCCAAGGAATACGGCCATCACCGGAGGGCCAGGATGAGTTGCC
LeuTrpAspValTyrAsnGlnTyrHisMetGlyIleThrAlaGluValAlaLysGluTyrGlyIleThrArgGluAlaGlnAspGluPheAla
```

```
                                                                      670
                       610                           650               .
       590              .                             .               GACCCG
        .              CAGAAGGCCGGGCAGAAGATGTCCCGGTGCTGATCCCGCAGGCCAAGG
GTCGGCTCGCAGAACAAGGCCGGC                                               GlyAspPro
        GlnAsnLysAlaGluAlaAlaGlnLysAlaGlyLysPheAspGluIleValProValLeuIleProArgLys
ValGlySer 750
                       710                           .
         690            .                           CAAGGGCCACGGTGACC
          .            GACAGCATGTCCGGCCTTCAAGCCCCTTC
GTGGCCTTCAAGACCGACGAGTTCGTGCCGCCAGG                     AspLysAlaGlyThrValThr
        PheLysThrAspGluPheValProAlaArgGlnGlyLeuLysProAlaPhe
ValAlaPhe                                                                    850
                                                                              .
                       790                            830
 770                    .                              .                CCTGGCCACG
  .                    AACGACGGCCAAGGCCAAGGAACTGGGCCTGCTGACCCCG  AlaThr
GCGGCCAACGCCCTCGGGCCTG           AlaAlaLysAlaAlaLysGluLeuGlyLeuGlyLeuThrProLeu
         AlaSerGlyLeuAsnAspGlyAlaAlaVal Val
AlaAlaAsn
                                                                                          Ava
                                                     910             930             950    .
                       870             890                                                  CGACC
                        .               .               TCCCGCCGCCCTCTCCGCCGGCCGGGCCGACTGGACC
                                        AGGTGTCGATCCCAAGCGCCCCGGTGGATGG                TrpThr
                        CTATGCCAACCGCCGGT              GluAlaGlyMetGlyProValProAlaSerArgAlaGluTrp
ATCAAGAGC                             AlaAsnAlaGlyIleValAspProLysVal Met
         SerTyr
IleLys
                                                      1050
                       990              1030            .                      CTTCAAGTCAAT
                       .                  .             GCCGGTGCACCAGCAGATGGGCTGGACACCTCA     ValAsn
           CCTGATGAGAGATCAACGAGAGGCCTTTGC                             TrpAspThrSerLys
                                GluIleAsnAlaGlnAlaLeuAlaValHisGlnAlaMetGly
CCGCAAGACCTG          AlaLeu
         LeuAspMetGluIle
ProGlnAsp 1130             1150
       1070             1090               1110             .                  .    GCCG
         .                .                   .           CTGCTGACCGTGCTGACGAGATGAAGGCCCTGACGCG
                             CACCCGGCCGGAGCGCGTCGGGGCTCCG          ValThrLeuLeuHisGluMetLysArgArgAspAla
GTGAACGGCGGCCATCGGCCACCGG                CysArgIleLeuVal
                               GlyHisProIleGlyAlaSer
                   AlaIleAlaIleGlyHis
ValAsnGlyGly
```

```
         1170            1190            1210            1230
AAGAAGGGCCTGGCCTGTGCATCGGCGTGATGGGCGGAGTGCGCGAGTCGAGGCAATAAGGAAGGGGTTTCGGGGCCGCCGCG
LysLysGlyLeuAlaSerLeuCysIleGlyGlyMetGlyValAlaLeuAlaValGluArgLys *
      1260            1280            1300            1320            1340
      Ava                                       Dde
GTTGGGCGGACCCGGCACGATAACGAAGCCAATCAAGGAGTGGACATGACTCAGCCCATTGCTTATGTGACCGGCGGATGGTGTATCGGA
                                  MetThrGlnArgIleAlaTyrValThrGlyMetGlyIleGly
1440    1360            1380            1400            1420
ACCGGCCATTTGCCAGGCTGGCCAAGGATGCTTCGTGTGGTGGCCGTTGCCGCCCAACTCGCCGCCGAAAAGTGCTGAGCAGCAG
ThrAlaIleCysGlnArgLeuAlaLysAspGlyPheArgValValAlaGlyCysGlyProAsnSerProArgArgGluLysTrpLeuGluGlnGln
         1460            1480            1500            1520
AAGGCCCTGGCTTCGATTCATTGCCTCGGAAGGCAATGTGCTGACTGGCAGCAAGACCCATTCGACAAGCTCAAGTCCGAGGTCGGC
LysAlaLeuGlyPheAspPheIleAlaSerGluGlyAsnValAlaAlaAspTrpAspSerThrLysThrPheAlaPheLysValLysSerGluValGly
1540            1560            1580            1600            1620
GAGGTTGATGTGCTGATCAACAACGCCGTATCACCCGGACGTGGTGTTCCGAAGATGACCCGGCCAAGATGACCCGGACTGGATGCGGTGATGATGACCAAC
GluValAspValLeuIleAsnAlaGlyIleThrArgAspValPheArgLysMetThrArgAlaAspTrpAspAlaValIleAspThrAsn
         1640            1660            1680            1700            1720
CTGACCTCGCTGTTCAACGTCACCAAGCAGGTGATCGACGGCATGCCGACCCGTGGCCCATCGTCAACATCTCGTCGGTGAACGGCAG
LeuThrSerLeuPheAsnValThrLysGlnValIleAspGlyMetAlaAspArgGlyTrpGlyArgIleValAsnIleSerSerValAsnGlyGln
         1740            1760            1780            1800            1820
AAGGGCCAGTTCGGCCAGACCAACTACTCCACCGCCAAGGCCGCTGCCATGGCTTCACCATGGCCACTGGGCCAGGAAGTGGCGACCAAGGGCGTG
LysGlyGlnPheGlyGlnThrAsnTyrSerThrAlaLysAlaGlyLeuHisGlyPheThrMetAlaLeuAlaGlnGluValAlaThrLysGlyVal
         1840            1860            1880            1900
ACCGTCAACACGGTCTCTCCGGGCTATATCGCCACCGACATGGTCAAGGCCGATCGCCAGGACGTCGACAAGATCGTCGACGATCCCGGTC
ThrValAsnThrValSerProGlyTyrIleAlaThrAspMetValLysAlaIleArgGlnAspValLeuAspLysAlaThrIleProVal
```

```
1920                1940                1960                1980                2000
   .                   .                   .                   .                   .
AAGGGCCTGGGCCTGCCGGAAGAGATCGGCCTGATCGCGGCCTGTTGTCTCGGAGGAGTCCGGTTTCTCGACCGGCCGACTTCTCGCTCAAC
LysArgLeuProGluGluIleAlaSerIleAlaCysAlaTrpLeuSerGluSerGlySerThrGlyAlaAspPheSerLeuAsn 2020                2040                2060                2080                2100
        .                   .                   .                   .                   .
GGCGGCCTGCATATGGGCTGACCTGCCGGGCCTGGTTCAACCAGTGGGCCCCCGGCTGGGCCCCCGTATTGCGGTCAGCCAGCGGCGGCACA
GlyGlyLeuHisMetGly *

2120                2140                2160                2180                2200
            .                   .                   .                   .                   .
AGGCGGGGCGGTTTCGTTCGCGCCGGCGTTTCGCCGGCGTCAAGGCCCGTCAAGGCCCCGAATCGTTTCTGCCCGGCATTCCTCGCTTTTGCGCCAAT 2220                2240                2260                2280                2300
                .                   .                   .                   .                   .
TCACCGGGTTTCCTTAAGCCCCGTCGCTTTCTTAGTGCCTTGTTGGGCATAGAATCAGGGCGGCAGCCAGCACCATGTTCGTGCAGCGC

2320   Pst
                    .
             GGCCCTCGCGGGGGCGAGCTGCAG
```

| | Monomer to be Polymerized by Enzyme | | Proposed Repeated Unit | |
|---|---|---|---|---|
| 1 | 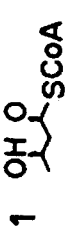 | D-3-OH-butyryl-S-CoA | → 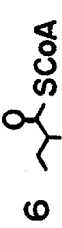 | C$_4$-methyl branched unit (1,3-ester link) |
| 2 | 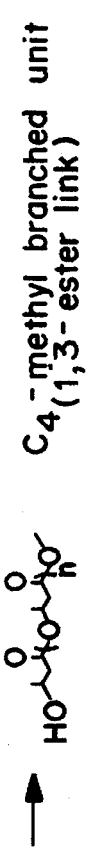 | D-2-OH-butyryl-S-CoA | → 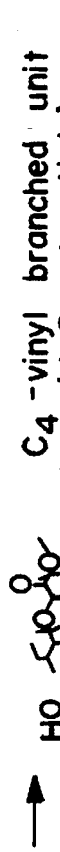 | C$_4$-ethyl branched unit (1,2-ester link) |
| 3 | 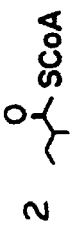 | 4-OH-butyryl-S-CoA | → 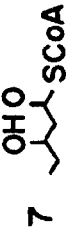 | C$_4$-linear unit (1,4-ester link) |
| 4 | 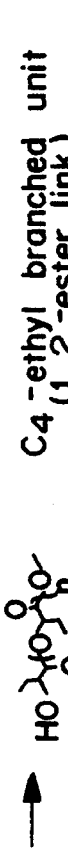 | D-3-OH-valeryl-S-CoA | → 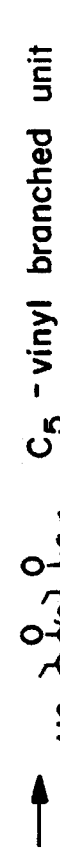 | C$_5$-ethyl branched unit (1,3-ester link) |
| 5 |  | D-2-OH-valeryl-S-CoA | → 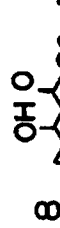 | C$_5$-propyl branched unit (1,2-ester link) |
| 6 | 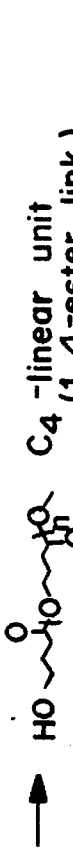 | D-2-OH-butenyl-S-CoA (vinylglycolyl) | → 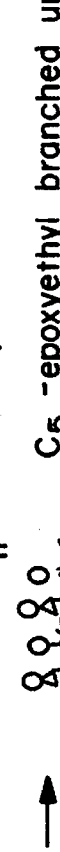 | C$_4$-vinyl branched unit (1,2-ester link) |
| 7 |  | D-3-OH-pentenyl-S-CoA | → 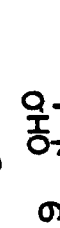 | C$_5$-vinyl branched unit (1,3-ester link) |
| 8 |  | D-3-OH-4,5-epoxy pentyl-S-CoA | → 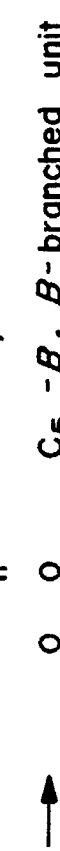 | C$_5$-epoxyethyl branched unit (1,3-ester link) |
| 9 | 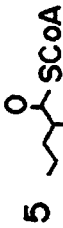 | 3,3-dimethyl-3-hydroxy-valeryl CoA | → 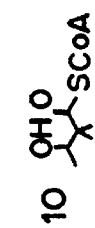 | C$_5$-$\beta,\beta$-branched unit (1,3-ester link) |
| 10 | 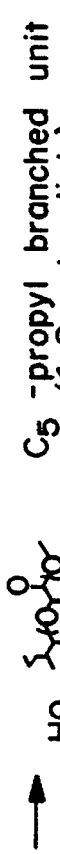 | 2,2-dimethyl-3-hydroxy-valeryl CoA | → 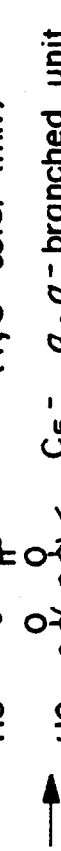 | C$_5$-$\alpha,\alpha$-branched unit (1,3-ester link) |

GENE ENCODING BACTERIAL BETA-KETOTHIOLASE

This is a divisional of U.S. Ser. No. 08/297,667 entitled "Gene Encoding Bacterial Acetoacetyl-Coa Reductase" filed on Aug. 29, 1994, now U.S. Pat. No. 5,512,669, by Oliver P. Peoples and Anthony J. Sinskey, which is a continuation of U.S. Ser. No. 08/124,570 filed on Sep. 20, 1993, now abandoned, which is a continuation of U.S. Ser. No. 07/944,488 filed on Nov. 3, 1992, which is a divisional of U.S. Ser. No. 07/566,535 filed on Aug. 13, 1990, now U.S. Pat. No. 5,229,279, which is a continuation of U.S. Ser. No. 07/067,695 filed on Jun. 29, 1987, now abandoned.

This invention was made with government support under Grant Number NIH-5-R01GM33039 awarded by the National Institutes of Health and Contract Number N0014-87K-0378 by the Navy. The government has certain rights in the invention.

BACKGROUND OF THE INVENTION

Synthesis by bacteria has long been the only means for production of many of the more complex biopolymers. Only recently have pathways for the synthesis of these polymers been determined. Much effort has gone into the isolation of the various enzymes and cofactors involved in these pathways. Regulation of their expression has largely been empirical, i.e., the concentration of nutrients or other factors such as oxygen level have been altered and the effect on polymer production and composition measured.

In order to have control over the production of these complex biopolymers, and to modify them in a controlled fashion, it is necessary to design a system for determining the chemical steps required for their synthesis; isolate and characterize the proteins responsible for these chemical steps; isolate, sequence, and clone the genes encoding these proteins; and identify, characterize, and utilize the mechanisms for regulation of the rate and level of the expression of these genes.

Polyhydroxybutyrate, a commercially useful complex biopolymer, is an intracellular reserve material produced by a large number of bacteria. Poly-beta-hydroxybutyrate (PHB), the polymeric ester of D(-)-3-hydroxybutyrate, was first discovered in *Bacillus megaterium* in 1925. Both the chemical and physical properties of this unique polyester have made it an attractive biomaterial for extensive study. PHB has a variety of potential applications, including utility as a biodegradable/thermoplastic material, as a source of chiral centers for the organic synthesis of certain antibiotics, and as a matrix for drug delivery and bone replacement. In vivo, the polymer is degraded internally to hydroxybutyrate, a normal constituent of human blood.

PHB accumulates inside the cell as discrete granules stainable with Sudan Black dye. The granules, which appear to be membrane bound, consist of approximately 98% PHB, 1–2% protein and approximately 0.5% lipid.

The enzymatic synthesis of the hydrophobic crystalline PHB granules from the $C_2$ biosynthon Acetyl-CoA has been studied in a number of bacteria. Three enzymes: beta ketothiolase, acetoacetyl-CoA reductase and PHB synthetase, are involved in the conversion of Acetyl-CoA to PHB, as illustrated in FIG. 1.

Beta-Ketothiolase (acetyl-CoA-CoA-C-acetyltransferase, E.C. 2.3.1.9) has been studied in *A. beijerinckii* (Senior and Dawes, *Biochem. J.*, 134, 225–238(1973)), *A. eutrophus* (Oeding and Schlegel, *Biochem. J.*, 134, 239–248 (1973)), *Clostridium pasteurianum* (Bernt and Schlegel, *Arch. Microbiol.*, 103, 21–30(1975)), and *Z. ramigera* (Nishimura et al., *Arch. Microbiol.*, 116, 21–27(1978)). However, the beta-ketothiolase enzyme has not been purified to homogeneity by any of these groups.

The best characterized Acetoacetyl-CoA reductase is that from Zoogloea, described by Saito et al., *Arch. Microbiol.*, 114, 211–217(1977) and Tomita et al., *Biochemistry of Metabolic Processes*, 353, D. Lennon et al., editors (Elsevier, Holland, 1983). This NADP-specific 92,000 molecular weight enzyme has been purified by Fukui, et al., to homogeneity, although only in small quantities.

PHB polymerase is not well characterized at present. When Griebel and Merrick, *J. Bacteriol.*, 108, 782–789 (1971) separated the PHB polymerase from native PHB granules of *B. megaterium* there was a complete loss of enzyme activity. They were able to reconstitute activity only by adding PHB granules to one of two fractions of the protein. More recently, Fukui et al., *Arch. Microbiol.*, 110, 149–156(1976) and Tomita et al. (1983), investigated this enzyme in *Z. ramigera* and partially purified the non-granule bound PHB polymerase.

Despite the diversity of the producing organisms, the composition and structure of the PHB polymer remain constant. In contrast, the molecular weight is reported to vary from species to species, ranging from 50,000 to 1,000,000 Daltons. The intrinsic or extrinsic mechanisms that determine this aspect of the polymer synthesis are still unclear.

PHB biosynthesis is promoted under a variety of nutrient limiting conditions. For example, *Azotobacter beijerinckii*, a nitrogen fixing bacteria accumulates up to 70% dry cell weight as PHB when grown on glucose/ammonium salts under limiting oxygen. Increasing the available oxygen leads to a decrease in PHB synthesis and a concomittant reduction in the levels of two of the biosynthetic enzymes. The reduction in enzyme levels is indicative of a regulatory mechanism(s) operating at the genetic level. Nitrogen limitation of the growth of *Alcaligenes eutrophus* results in yields of up to 80% dry cell weight PHB. Similarly, Halobacterium and Pseudomonas sp. increase PHB production under nitrogen limitation. Determining the mechanisms by which PHB synthesis is stimulated could lead to novel control strategies for synthesis of PHB.

Given the extremely high yields of this polymer obtainable through classic fermentation techniques, and the fact that PHB of molecular weight greater than 10,000 is useful for multiple application, it is desirable to develop new PHB-like biopolymers to improve or create new applications. Different PHB-like polymers with altered physical properties are occasionally synthesized by bacteria in nature. In general, the bacteria incorporate monomers other than D(-)hydroxybutyrate into the final polymer product. These alternate substrates are presumably incorporated through the enzymes of the normal PHB biosynthetic pathway. Unfortunately, it is difficult to study the biosynthesis of these polymers since they are produced under uncontrolled conditions by an indeterminate number of bacterial species.

The production of poly-beta-hydroxyalkanoates, other than PHB, by monocultures of *A. eutrophus* and *Pseudomonas oleovorans* has recently been reported by deSmet, et al., in *J. Bacteriol.*, 154, 870–878(1983) and Senior, et al., Eur. Patent Appl. 86303558.0. In both bacteria, the polymers were produced by controlled fermentation. *A. eutrophus*, when grown on glucose and propionate, produces a heteropolymer of PHB-PHV poly B-hydroxyocleic acid, PHV content reaching approximately 30%. *P. oleovorans* produces a homopolymer of poly-beta-hydroxyoctanoate when grown on octane. Nocardia has been reported to form copolymers of PHB-PH-2-butenoate when grown on n-butane. Determination of the final composition of 3-hydroxybutyrate polymers by controlled fermentation using selected substrates is also disclosed in U.S. Pat. No. 4,477,654 to Holmes et al.

Despite the great interest in synthesis of biopolymers and especially PHB, the mechanism and genetics of how the biosynthesis of heteropolymers occurs is unknown. To date, the only genetic studies on PHB synthesis have been limited to isolation of PHB-mutants of A. eutrophus by Schlegel et al., Arch. Microbiol. 71, 283–294 (1970).

It is therefore an object of the present invention to provide a method for determining the chemical steps required for synthesis of complex biopolymers, particularly PHB and PHB-like polymers, for isolating and characterizing the proteins responsible for these chemical steps, for isolating, sequencing, and cloning the genes encoding these proteins, and for identifying, characterizing, and utilizing the mechanisms for regulation of the rate and level of the expression of these genes.

It is another object of the present invention to provide purified proteins expressed from the genes encoding the proteins for synthesis of poly-hydroxybutyrate.

It is still another object of the present invention to provide sequences regulating the expression of the genes encoding the proteins required for biopolymer synthesis.

It is a further object of the present invention to provide methods for using these proteins and regulatory sequences to create novel biopolymers having polyester backbones.

SUMMARY OF THE INVENTION

The present invention is a method for controlling biopolymer synthesis by determining the genetics and enzymology of polyhydroxybutyrate (PHB) biosynthesis at the molecular level. The purified enzymes and genes provide the means for developing new polyester PHB-like biopolymers. Specific aims are to 1) control the chain length of the polymers produced in fermentation processes through genetic manipulation, 2) incorporate different monomers into the polymers to produce co-polymers with different physical properties, and 3) examine the physical/rheological properties of these new biopolymers in order to develop further design criteria at the molecular level.

The method for engineering biopolymer synthesis includes: isolation and characterization of the genes for the enzymes in the synthetic pathway (beta-ketothiolase, acetoacetyl-CoA reductase and PHB polymerase); cloning of the genes in a vector(s); placement of the vector(s) under the control of regulated promoters; expression of the genes; determination of the function and use of other factors such as substrate specificity in polymer production and composition; and isolation and physical and chemical analysis of the resulting polymers.

Genes from Gram negative organisms, Zoogloea ramigera strain I-16-M, Alcaligenes eutrophus and Nocardia salmonicolur, were identified or isolated and used to study the PHB biosynthetic pathway.

BRIEF DESCRIPTION OF THE DRAWINGS

FIGS. 3a and 3b is the Zoogloea thiolase gene sequence. The sequences located at positions hemologeous to the E. coli "–10"0 and "–35" concensus regional (–100 to –95 and –122 and –116) upstream from the transcription start site (bold arrow) are underlined. A probable ribosome binding site is underlined (–11 to –8).

FIG. 4 is a diagram of the extent of the 5' deletions in plasmid constructs pZT3–pZT3.5.2 and thiolase specific activity (units/mg protein) expressed following induction of tac-directed expression.

FIG. 5 is a diagram of the construction of reductase expression plasmids pZT1, pZT2 and pZT3.

FIG. 6a and 6b are is the complete nucleotide sequence of the a2.5 Kb of Z. ramigera DNA located downstream from the thiolase gene in clone pUCDDK1. The sequence of 2094bp extending from the first Sal 1 site to the second Sma 1 site is shown. Also shown is the translation product of the acetoacetyl-CoA reductase structural gene extending from the ATG at nucleotide 37 to the TGA stop codon at nucleotide 760. Amino acid residues 2 to 6 are underlined. These amino acids are identical to those obtained by Edman degradation of the purified protein. Restriction sites for Sal 1 and Sma 1 are shown.

FIG. 7 is a diagram of the construction of overproduction vectors pAT and pAR.

FIGS. 8 a, 8b, 8c, and 8d shows the nucleotide sequence of the 2 Kb fragment A. eutrophus DNA cloned in plasmid pAeT3. The translation products of the A. eutrophus thiolase and acetoacetyl-CoA reductase genes extending from nucleotides 40 to 1219 and 1296 to 2034, respectively, are shown. Restriction endonuclease cleavage sites used in the construction of the over production vectors pAT and pAR are shown. Pst 1=Pst 1; Ava=2 and Dde=Dde 1.

FIG. 9 are representative acyl thiolester substrates for PHB polymerase and the proposed repeating units in the resulting monomer.

DETAILED DESCRIPTION OF THE INVENTION

Figure 1:
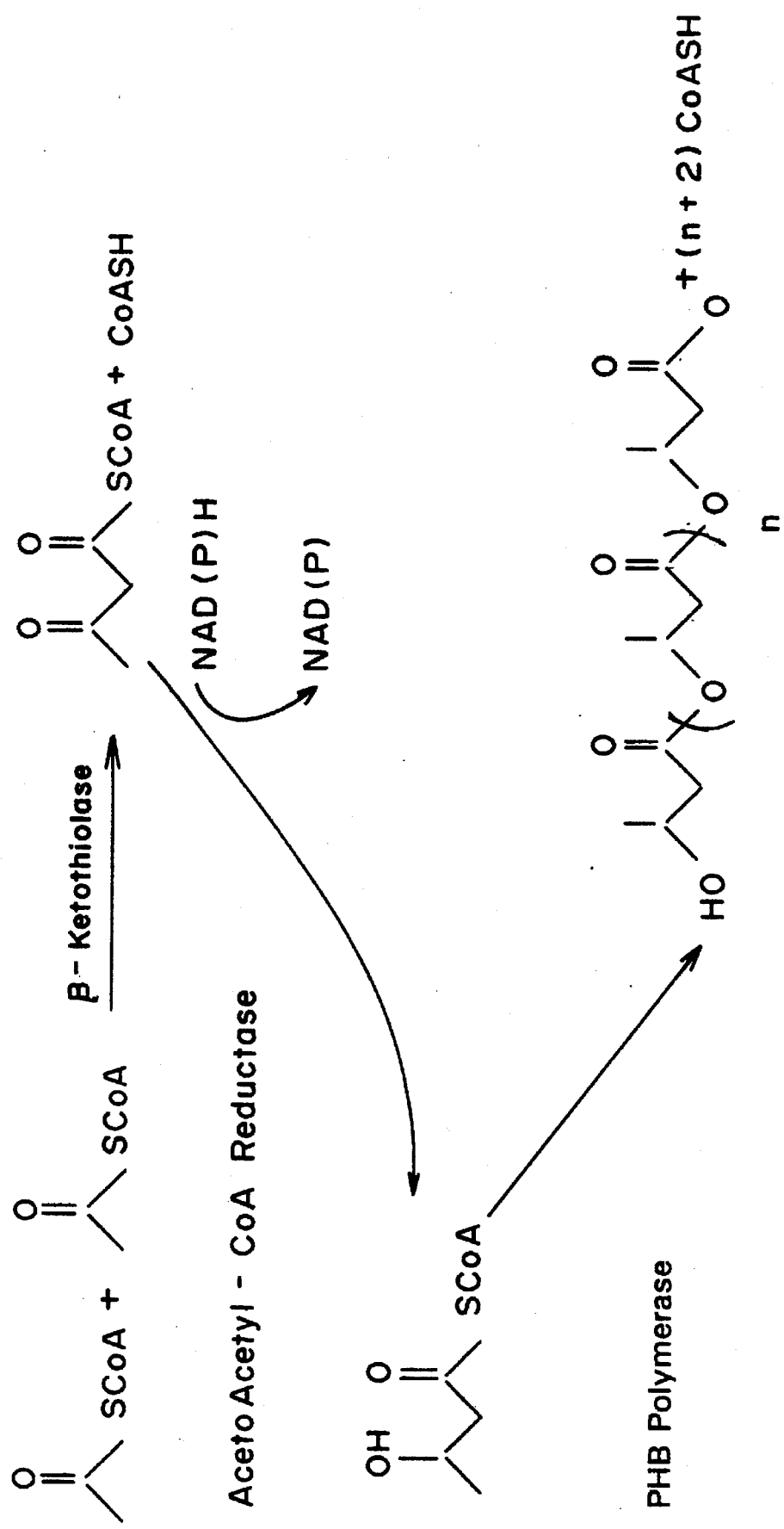
FIG. 1 is the PHB biosynthetic pathway.

Poly(beta-hydroxybutyrate) (PHB) is a unique biodegradable thermoplastic produced in a fermentation process. PHB has a number of interesting properties which make it an attractive material for the plastic and biomedical industries. One feature of PHB is that alternate polymers can be produced by carefully controlling the fermentation conditions. This, in addition to the well characterized biochemistry of the biosynthetic pathway, makes it a particularly useful system for demonstrating a method of biopolymer engineering using recombinant biotechnology.

There are three enzymes in Z. ramigera responsible for PHB synthesis: a thiolase, a reductase, and a polymerase. Thiolases are ubiquitous enzymes which catalyze the synthesis and cleavage of carbon-carbon bonds and thus occupy a central role in cellular metabolism. Different thiolase enzymes are involved in terpenoid, steroid, macrolide and other biosynthetic pathways as well as the degradation of fatty acids. The only thiolase genes cloned to date (from rat mitochondria and E. coli) have been for thiolases involved in fatty acid degradation which are regulated at the level of gene expression. In Z. ramigera, the condensation of two acetyl-CoA groups to form acetoacetyl-CoA is catalyzed by beta-ketothiolase. The Acetoacetyl-CoA is then reduced by an NADP-specific reductase to form D(-)-beta-hydroxybutyryl-CoA, the substrate for PHB polymerase. The reductase involved in PHB biosynthesis in Z. ramigera is stereospecific for the D(-)-isomer of hydroxybutyryl-CoA and uses NADP(H) exclusively as a cofactor. The PHB polymerase in Z. ramigera is stereospecific for D-betahydroxybutyryl CoA. Polymerase from other bacteria such as *A. eutrophus* should utilize other substrates, for example, D-beta-hydroxyvaleryl CoA since addition of propionate into *A. eutrophus* cultures leads to incorporation of $C_5$ and $C_4$ units into a PHB/HV copolymer.

By combining these enzymes with the appropriate substrates under controlled culture conditions of available oxygen and temperature, a variety of polymers can be constructed. The enzymes or nucleotide sequences controlling their expression can also be modified to alter the quantity of expression or substrate specificity to further vary the resulting polymers. An added advantage to the present invention is that substrates which normally cannot be used with whole cells can be manufactured using the isolated enzymes.

The following methods are used to isolate genes encoding beta-keto thiolase, AcetoAcetyl-CoA reductase, and PHB polymerase and their expression products, to identify and characterize sequences regulating their expression, and to determine the effect of culture conditions and substrate availability on polymer production. Techniques for constructing systems for the production of PHB and PHB-like biopolymers are also disclosed.

Construction of a *Z. ramigera* Library

Zoogloea ramigera strain I-16-M was used initially to study the genetics of the PHB biosynthetic pathway. *Z. ramigera* DNA was purified from 200 ml mid-log phase cultures as follows: cells were harvested by centrifugation, washed in 20 mM Tris-HCl, pH 8.2, and resuspended in 10 ml of Tris-HCl. The cells were then spheroplasted by the addition of 10 ml of 24% w/v polyethylene glycol 8000 and 2 ml of 25 mg/ml lysozyme, followed by incubation at 37° C. for 30 min. The spheroplasts were harvested by centrifugation, resuspended in 5 ml of TE buffer (10 mMTris-HCl, pH 8.0, 1 mM EDTA), 300 microliters of 10% w/v SDS added, and the cells lysed by incubating at 55° C. for 10 min. An additional 10 ml of TE was added and the lysate incubated with RNAse (50 microgram/ml) and proteinase K (30 microgram/ml) for 1 h at 37° C. The DNA was then purified by CsCl gradient centrifugation.

Plasmid DNA preprations were carried out using the method of Birnboim and Doly in *Nucleic Acids Res.*, 7, 1513–1523(1979) as described by Ish-Horowicz and Burke, *Nucleic Acids Res.*, 9, 2989–2998(1981). Lambda DNA was prepared by standard procedures described in Maniatis et al., *Molecular Cloning: A Laboratory Manual*, (Cold Spring Harbor Laboratory, Cold Spring Harbor, N.Y. 1982).

A recombinant library of random *Z. ramigera* DNA fragments was constructed using the lambda gt11 expression vector described by Young and Davis, *Science*, 222, 778–782(1983). *Z. ramigera* DNA was first methylated using EcoRI methylase and then partially digested with DNAse1 in the presence of $Mn^{2+}$, as taught by Anderson, *Nucleic Acids*, 9, 3015–3026(1981). The ends of the partially digested DNA fragments were repaired using Klenow polymerase, EcoRI linkers added, and the DNA digested to completion with an excess of EcoRI. Fragments of 2–8 kb were size-selected on a 1.5% agarose gel, purified by electroelution, and ligated with EcoRI-digested, phosphatased lambda gt11 DNA. Ligations were carried out for 18 h at 4° C. using 2 micrograms of lambda gt11 DNA and 1 microgram of target DNA in a total volume of 10 microliters. The complete ligation reactions were packaged in vitro using lambda extracts prepared from *E. coli* strains BHB2688 and BHB2690, Hohn and Murray, *Proc. Natl. Acad. Sci. USA*, 74, 3259–3263(1977), as described by Maniatis et al. (1982). Packaged phage were plated out and amplified on *E. coli* Y1088.

Screening of the lambda gt11 expression library was carried out using rabbit anti-thiolase anti-bodies and a modification of the procedure described by Young and Davis, *Science*, 222, 778–782(1983).

Identification of the *Z. ramigera* Thiolase Gene

Thiolase antiserum was prepared in New Zealand White female rabbits, using purified thiolase protein by standard procedures. Antibody titer was estimated by the Ouchterlony double-diffusion assay, *Acta Pathol. Microbiol. Scand.*, 26, 507–515(1949). Purified antibody was prepared from the serum by chromatography on protein A agarose according to Bighee et al., *Mol. Immunol.*, 20, 1353–1357(1983). Approximately $4 \times 10^4$ recombinant phage adsorbed to *E. coli* Y1090 were plated out on 15 cm LB-agar plates and incubated at 42° C. for 3 h. The plates were then overlayed with nitrocellulose filters (Schleicher & Schull, BA85), which had previously been saturated in 10 mM IPTG, and incubated a further 4 h at 37° C. Filters were removed, washed for 10 min in TBST (50 mM Tris-HCl, pH 7.9, 150 mM NaCl, 0.05% Tween-20), incubated in TBST plus 20% v/v fetal calf serum for 30 min, and rinsed in TBST. First antibody was bound by incubating the filters in 10 ml TBST plus purified anti-thiolase antibody (10 microliters) for 1 h at room temperature. The filters were subsequently washed in three changes of TBST for 5 min each time. Bound first antibody was detected using a biotin-avidin horseradish peroxidase detection system (Clontech Laboratories) and horseradish peroxidase color development reagent (Bio-Rad Laboratories, Richmond, Va.).

Proteins were separated by sodium dodecyl sulphate-polyacrylamide gel electrophoresis according to the method of Laemmli, *Nature*, 222, 680–685(1970) and electrophoretically transferred to nitrocellulose filters (Schleicher & Schuill BA85), essentially as described by Burnette, *Anal. Biochem.*, 112, 195–203(1981). Following transfer overnight at 30 V, filters were rinsed in TBS (TBST without Tween-20) and incubated in TBS plus 5% bovine serum albumin. Proteins reacting with anti-thiolase serum were then detected by incubating the filters in 100 ml of TBS, 1% gelatin containing 2 ml of anti-thiolase serum for 1–2 h. Bound first antibody was subsequently detected using goat anti-rabbit IgG horseradish peroxidase conjugate and horseradish peroxidase color development reagent (Bio-Rad Laboratories, Richmond, Calif.).

DNA blots were prepared using DNA fragments separated on agarose gels by the sandwich blot method of Smith and Summers, *Anal. Biochem.*, 109, 123–129(1980) based on the technique developed by Southern, *J. Mol. Biol.*, 98, 503–517 (1975). Filters were hybridized with DNA probes labeled to a high specific activity ($0.1 – 1 \times 10^8$ cpm/microgram of DNA) with [alpha-$^{32}$P]dATP, by nick translation, Rigby et al., *J. Mol. Biol.*, 113, 237–251(1977). Prehybridizations and hybridizations were carried out at 65° C. in sealed polythene bags. The prehybridization/hybridization solution contained 5×SSCP (1×SSCP contains 0.15M NaCl, 0.15 M sodium citrate, 10 mM $Na_2HPO_4$, 10 mM $NaH_2PO_4$), 5×Denhardt's solution, 0.1% (w/v) SDS, 10 mM EDTA, and 100 microgram/ml sonicated denatured salmon DNA. Filters were prehybridized for 8–18 h and hybridized for 16–18 h using $10^7$ cpm of labeled DNA probe per filter.

Lysogens of lambda gt11 recombinant clones were prepared in *E. coli* Y1089 as described by Young and Davis, *Science* 222, 778–782 (1983). For the preparation and analysis of lambda-coded proteins, lysogens were grown at 30° C. in LB (100 ml) until they reached an $OD_{600}$ of 0.5. The prophage was induced by a 20 min incubation at 45° C., IPTG added to 5 mM and the induced lysogens incubated at 37° C. for 1 h. Cells were harvested, resuspended in assay buffer (0.1M Tris-HCl, pH 7.5, 5 mM beta-mercaptoethanol, 5% (v/v) glycerol), lysed by sonication, cell debris pelleted by centrifugation, and the cell extracts stored at −20° C. The protein concentrations of bacterial lysates were assayed by the method of M. M. Bradford in *Anal. Biochem.* 72, 248–254 (1976), using bovine serum albumin as a standard. Thiolase-enzyme assays were performed as described by Nishimura et al., *Arch. Microbiol.* 116, 21–27 (1978).

DNA fragments were cloned into the M13 vectors mp10 and mp11 and sequenced by the dideoxy chain-termination method of Sanger et al., *Nucleic Acids Res.* 10, 141–158 (1980), *Proc. Natl. Acad. Sci. USA* 74, 5463–5467 (1977). The M13 sequencing primer and other reagents were purchased from Amersham Corp. G/C rich regions were resequenced using dITP in place of dGTP as described by Mills and Kramer, *Proc. Natl. Acad. Sci. USA* 76, 2232–2235 (1979). Computer-assisted sequence analysis was accomplished using the Staden programs. (*Nucleic Acids Res.* 10, 141–158 (1984).

Approximately $2\times10^5$ recombinants were obtained from 1 microgram of purified target DNA, and amplified in *E. coli* Y1088. A total of $10^5$ amplified phage were screened using purified rabbit anti-thiolase antibodies. The initial screening identified 10 potentially positive clones (LDBK1-LDBK10). Analysis by restriction digestions demonstrated that clones LDBK2–10 are identical. Clones LDBK1 and LDBK2 were selected for further study. LDBK1 has an insert composed of 2 EcoRI fragments of 3.6 kb and 0.75 kb. LDBK2 has an insert composed of 3 EcoRI fragments of 1.65 kb and 1.08 kb.

The proteins coded for by the LDBK1 and LDBK2 insert sequences were analyzed both for thiolase-enzyme activity and for cross-reaction to rabbit anti-thiolase serum. Lysogenic strains of *E. coli* Y1089 containing LDBK1 and LDBK2 phage DNA were prepared. Several lysogens were obtained for each clone and two of these, Y1089/LDBK1 and Y1089/LDBK2, were used for subsequent studies. A lysogen of the lambda gt11 vector, BNN97/lambda gt11, was used as a control. The results of the thiolase-enzyme assays clearly indicate that the proteins from Y1089/LDBK1 contain a substantial amount of thiolase activity. Furthermore, the thiolase activity is inducible, greater than 5-fold, by the addition of IPTG. This shows that expression of the thiolase-coding sequences is under the transcriptional control of the lac promoter contained in the lambda gt11 vector. Neither the Y1089/LDBK2 nor the BNN97/lambda gt11 protein lysates demonstrate any significant thiolase-enzyme activity even when induced with IPTG.

The size of the proteins responsible for the initial positive reaction to rabbit anti-thiolase antibodies was investigated by Western blot experiments. Protein lysates were separated by SDS-polyacrylamide gel electrophoresis, transferred to nitrocellulose filters, and screened with rabbit anti-thiolase serum. The results show an immuno-reactive 40,000 dalton protein in both the IPTG-induced and non-IPTG-induced lysate of Y1089/LDBK1.

Figure 2:
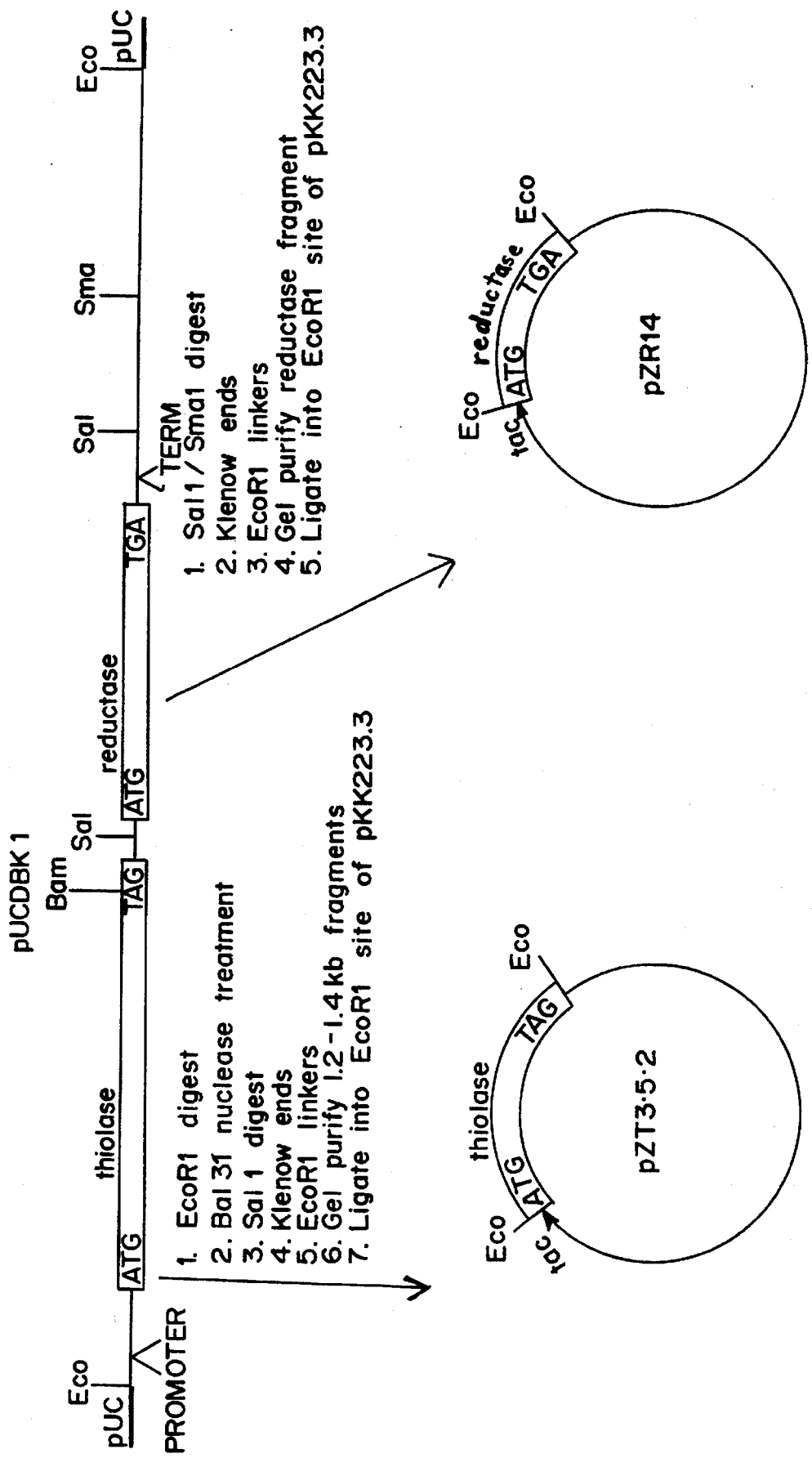
FIG. 2 is a restriction map of pUCDBK1 and diagram of the construction of pZT3.5.2 and pZR14.

The LDBK1 insert was restriction mapped. The large 3.6 kb EcoRI fragment, containing the complete thiolase gene region, was subcloned into the plasmid vector pUC8 for ease of manipulation. Restriction analysis of one of the subclones obtained, pUCDBK1, shown in FIG. 2, confirmed the restriction map of this fragment in LDBK1. pUCDBK1 DNA was labeled to a high specific activity with $^{32}$p and hybridized to nitrocellulose filters containing *Z. ramigera* chromosomal DNA digested with the same enzymes used to restriction map pUCDBK1. Southern hybridization experiments confirm that the 5.4 kb genomic fragment hybridizes to both a 1.45 kb SalI/EcoRI and 1.05 kb SalI fragment from pUCDBK1. Based on the result of Southern hybridization experiment, the cloned pUCDBK1 insert is represented in the *Z. ramigera* genome only once.

DNA sequence analysis of the pUCDBK1 insert was carried out using the M13/Sanger dideoxy chain termination method. To locate the gene-coding region, individual DNA sequences were scanned in all six reading frames for homology to the NH$_2$-terminal amino acid sequence. By using this approach, the gene-coding region within the 1.46 kb EcoRI-Sal/I fragment was identified. The complete nucleotide sequence of the plus strand of the gene is shown in FIGS. 3*a* and 3*b* 290 downstream from the EcoRI site lies the start of the thiolase structural gene, assigned by comparing the DNA sequence to the NH$_2$-terminal amino acid sequence. The NH$_2$-terminal sequence lies in the single long open reading frame which extends from position −89 to the stop codon (TAG) at nucleotide 1174. Beginning with a serine and extending for 25 residues, the experimentally determined NH$_2$-terminal sequence aligns identically with residues 2 through 26 of the translated DNA sequence. Translation of the DNA sequence was then used to deduce the remaining amino acid sequence from residue 27 to 391 (nucleotides 79 to 1173). Hence, translation of the DNA sequence from nucleotide 1 to 1174 (in this reading frame) encodes a 391-amino acid polypeptide with a calculated $M_r$ 40,598. This value is in very good agreement with that of $M_r$=42,000 determined by SDS-polyacrylamide gel electrophoresis.

Two additional pieces of evidence confirm that this translation produce is the correct amino acid sequence of thiolase. First, a search of the predicted amino acid sequence for the active site peptide (NH2—Gly—Met—Asn—Gln—Leu—Cys—Gly—Ser—Gly—COOH) located this peptide at residues 84–92. Finally, the predicted amino acid composition from the translation product and that determined experimentally are in excellent agreement. The G/C content of the 1.46 kb EcoRI-SalI fragment is high, 66.2%. When considered separately, the 5'-flanking 290 bp has a G/C content of 57.4% and the structural gene region 68.4%. The amino acid sequence confirms that the *Z. ramigera* thiolase contains 5 cysteine residues. The *Z. ramigera* active site cysteine is at residue Cys-89. Additional cysteines which may be involved in inter- or intradisulphide bonds are Cys-125, Cys-323, Cys-377, and Cys-387. NH$_2$-terminal sequence analysis indicated a serine at position 1.

Seven nucleotides upstream from the ATG start codon is a potential ribosome-binding site, 5'-CTGAGGA-3' identified by homology to the *E. coli* sequence. Additional start codons including two GTGs which can initiate translation in some bacterial genes are located further upstream. Examination of the 5'-flanking region for homology to the "−10" and "−35" *E. coli* promoter elements, identified a potential "−35' region at residues −122 to −116 and a corresponding "−10 region", 5'-TATAAT-3', at position −100 to −95. A poly(T) tract at position −255 to 31 266 is also present. It is clear that the only post-translational processing of thiolase is the removal of the N-formylmethionine residue, as alternate start codohs, ATC or GTG, are either out of frame or have an in-frame stop codon before the start of the structural gene.

The 1.5 Kb SalI-EcoR1 fragment from puCDBK1 contains the entire *Z. ramigera* thiolase structural gene plus 283 bp of 5'/flanking DNA. A series of plasmid constructions were made in which this DNA fragment was inserted into the tac promoter vector pKK223-3 (or derivatives thereof). pZT3 was made by cleaving pUCKBK1 with SalI, blunt-ending with Klenow polymerase and adding on EcoR1 linkers. Following digestion with EcoR1, the 1.5 Kb fragment was purified from an agarose gel and inserted into the EcoR1 site of pKK223-3. Recombinant clones having the gene inserted in the correct orientation with respect to the tac promoter were identified by restriction analysis following transformation of *E. coli* JM105.

A series of clones deleted of sequences in the 283 bp flanking the 5' end of the thiolase gene was then constructed. pUCDBK1 DNA was digested with EcoR1 and treated with Bal31 nuclease. Following Sal1 digestion, the ends of the fragments were repaired with Klenow and EcoR1 linkers added on. The plasmid DNA was cleaved with EcoR1 and fragments in the correct size range, 1.2–1.4 Kb, purified from an agarose gel and ligated into the EcoR1 site of pKK223-3. Clones of interest were identified by restriction mapping and the extent of the 5'-deletion determined by DNA sequencing, diagrammed in FIG. 4. From this series of clones, pZT3.1–pZT3.5, the clone with the largest deletion, pZT3.5, had 84 bp of the 5'-flanking DNA remaining and therefore a subsequent Bal31 deletion experiment was carried out as follows: pZT3.5 DNA was digested to completion with EcoR1 and treated with Bal31 nuclease; the ends were repaired using Klenow polymerase and EcoRI linkers ligated on, following digestion to completion with EcoR1 and BamH1, fragments corresponding to the NH$_2$-terminal region of thiolase were eluted from an agarose gel, ligated with BamH1–EcoR1 digested M13 mp 11 DNA and plated out on *E. coli* JM101; single-stranded DNA was prepared from 50 transformants and the extent of the 5'-deletion analyzed by T-tracking; double-stranded DNA was prepared, in vitro, from clones of interest and the EcoR1 –Bam1 inserts recovered by restriction digestion and elution from an agarose gel.

In order to reconstruct the intact thiolase gene, the 290 bp BamH1–HindIII fragment from pZT3.5 was ligated into a vector (pKK226) derived from pKK223-3 by deleting the BamH1 site upstream from the tac promoter; this C-terminal vector was subsequently used for the reconstruction of the Bal31 deleted NH$_2$-termini of interest; clones pZT3.5.1 and pZT3.5.2 were used in subsequent studies.

The effect of deleting sequences in the 283 bp of DNA flanking the thiolase ATG translation initiation codon was determined by analyzing the level of thiolase activity produced by plasmids pZT3.1–pZT3.5.2. 100 ml cultures of the *E. coli* JM105 containing each plasmid were induced with IPTG for 15 hours and the level of thiolase assayed. FIG. 4 presents the results of this series of experiments and illustrates the extent of the 5'-deletions for each plasmid. The most notable feature of these results is the very high level of thiolase expression obtained with clones, pZT3.3–pZT3.5.2, the maximum obtained being 178 u/mg for pZT3.5. This represents an increase of 5.9-fold as compared to plasmid pZT3 which contains the entire 283 bp of 5'-flanking DNA. The data presented in FIG. 4 demonstrate that the thiolase 5'-flanking sequences located between –84 (pZT3.5) and –168 (pZT3.2) strongly inhibit the expression of the thiolase gene from the tac promoter. Furthermore, the location of these sequences can be narrowed down to the region between –84 (pZT3.5) and –124 (pZT3.4) as the deletion of this region results in the maximum level of tac-directed thiolase expression. Further deletions to –37 (pZT3.5.1) and –26 (pZT3.5.2) do not increase the level of thiolase expression, and in fact a slight decrease is observed. It is important to note that the time course of induction for this series of clones follows the same kinetics as pZT3 and is not appreciably affected by the deletions.

In order to determine if the thiolase promoter lies in the region –84 (pZT3.5) to –124 (pZT3.4), S1 nuclease protection experiments were carried out according to the method of Berk and Sharp, *Cell* 12, 721–732 (1977) on *Z. ramigera* RNA. The RNA was isolated from a 100 ml mid-log phase culture by the hot phenol/glass beads extraction procedure of Hinnenbusch et al., *J. Biol. Chem.* 258, 5238–5247 (1983). 5'-$^{32}$P-labelled DNA probe was prepared as follows: 10 micrograms, plasmid pZT3.1 DNA was digested to completion with AvaI and subsequently treated with CIP; the AvaI restriction fragments were labelled at the 5'-end with [gamma-$^{32}$P]-ATP and polynucleotide kinase; following EcoR1 digestion, the DNA was separated on an 8% acrylamide gel and the $^{32}$P-labelled 280 bp probe fragment eluted and recovered by ethanol precipitation. Probe (10,000 cpm) and 11 microgram RNA were pooled, freeze dried, resuspended in 10 microgram hybridization buffer (40 mM pipes, pH 6.4; 1 mM EDTA, pH 8.0; 0.4 M NaCl; 80% (v/v) formamide), denatured for 10 min at 90° C. and annealed at 55° C. overnight. 235 microliters ice-cold S1 nuclease buffer (0.25 M NaCl; 30 mM NaOAc; 1 mM ZnSO$_4$; 200 micrograms single stranded calf thymus DNA) containing 2000 units of S1-nuclease was added followed by an incubation at 37° C. for 30 min. The reaction mixture was extracted once with phenol-chloroform and ethanol precipitated in the presence of 0.2M NaOAc and 10 micrograms. yeast tRNA carrier. The resulting fragments were analyzed on a 6% (w/v) acrylamide, 7M urea DNA sequencing gel. For size standards, the Maxam Gilbert G and C sequencing reactions were performed on 50,000 cpm of 5'-$^{32}$P-labeled probe DNA. The results clearly show a protected fragment and that the RNA start site is located at the C or T residue, position –86 or –87. A control indicates that in the absence of *Z. ramigera* RNA, the probe is completely degraded, demonstrating the presence of the thiolase promoter regions approximately 10 bp (–96) and 35 bp (–121) upstream. The 5'-untranslated region of the thiolase is 86 bp long.

From the results of the induction experiments, it is clear that the thiolase gene can be expressed at high levels in a soluble, catalytically active form in *E. coli*. S1-nuclease studies map the transcription start site for the thiolase gene in *Z. ramigera* at nucleotides –86/–87.

A possible explanation of the inhibitory effect of the thiolase promoter region on tac-directed expression can be proposed based on the assumption that both promoters are recognized by RNA polymerase equally but initiate transcription at very different rates. In this respect it is noted that the "–35" region of the thiolase promoter is very similar to the *E. coli* consensus sequence yet the thiolase "–10" region does not closely resemble the TATAAT box, as shown in FIG. 3a and 3b. Studies have demonstrated that although the "–35" region is recognized and binds the RNA polymerase, it is the "–10" region which determines the rate of transcription initiation. In the case of pZT3, for example, the binding of an RNA polymerase molecule to each promoter at the same time would result in the rapid initiation of transcription from the tac promoter which would subsequently be impeded by the presence of the polymerase molecule bound at the Zoogloea promoter. A consequence of this explanation is that the closer the two promoters are linked, the less chance of polymerase binding to both at the same time and the lower the inhibition. Therefore, this represents one means for controlling rate of expression of the enzyme.

Identification of the *Z. ramigera* Reductase Gene

After identifying the promoter region of the thiolase gene and noting the absence of any potential terminator sequences downstream from the thiolase TAG stop codon, the remaining 2 kb of Zoogloea DNA present in clone pUCDBK1

(FIG. 2) was sequenced and examined for the reductase gene. A series of expression plasmids (pZT1-pZT3) containing either the entire pUDCBK1 insert or fragments thereof were constructed in the E. coli tac promoter vector pKK223.3, as diagrammed in FIG. 5. Each plasmid has the thiolase gene located in the correct orientation for expression from the tac promoter. It is reasonable to expect the tac promoter to direct not only thiolase expression but the expression of any genes located in the 2.3 kb downstream in an operon-like type organization. Clone pZT1 was constructed by inserting the entire 3.8 kb EcoR1 Z. ramigera DNA insert from pUCDBK1 into the EcoR1 site of the vector pKK223-3. Subsequently, pZT2 was derived from pZT1 in a straightforward manner by deleting the 850 bp SmaI fragment. pZT3 is constructed as described for the identification of the thiolase promoter. A series of tac promoter induction experiments were performed on each of the recombinant clones pZT1, pZT2 and pZT3. The vector pKK223-3 was used as a control.

E. coli cells containing each of the plasmids was grown and induced by the addition of isopropyl-beta-D-galactopyranoside (IPTG) to a final concentration of 2 mM. After 15 h induction, 10 ml cultures were harvested and lysed by sonication. The cell lysates from each clone were then analyzed both by enzyme assay and on SDS-PAGE. No PHB polymerase activity was detected in any of these lysates. Each of the three recombinant plasmids pZT1, pZT2 and pZT3 demonstrate substantial levels of thiolase activity. In addition, the lysates from pZT1 and pZT2 have comparably high levels of AcAc-CoA reductase activity using NADPH as the cofactor. No reductase activity is detected in any of the lysates when NADH is used as a cofactor. The control, pKK223-3, has neither thiolase nor reductase activities. To confirm that the lysates from pZT1 and pZT2 do in fact contain the correct reductase, these lysates were also assayed for oxidation of D(-)-hydroxybutyryl-CoA. In both cases, enzyme activity was observed with NADP as electron acceptor.

Each of the lysates described above was also analyzed by SDS-PAGE. The result clearly show the presence of the thiolase protein at around 42,000 daltons in protein lysates from pZT1, pZT2 and pZT3, which is not present in the control, pKK223-3. Lysates of pZT1 and pZT2 also have a small, 25,000 dalton protein which is not present in the lysate pZT3 or the control, assumed to be the AcAc-CoA reductase as the basis of the recent report by Fukui et al., (1987) of a subunit molecular weight for the Z. ramigera AcAc-CoA reductase of 25,000. The results demonstrate that the AcAc-CoA reductase gene is located downstream from the thiolase gene. Furthermore, the entire structural gene for this enzyme must be located between the 3'-end of the thiolase and the first SmaI site downstream in pUCDBK1.

Identification of the Translation Start Site and Overexpression of the Reductate Gene The complete nucleotide sequence of the 2339 bp located 2.3 kb downstream from the first SalI site in pUCDBK1 is shown in FIGS. 6a 6b. Computer analysis of the sequence data, using codon usage information from the thiolase gene as a standard, identified three open reading frames. N-terminal protein sequence data was obtained from the 25,000 dalton band present in induced lysates from pZT1 and pZT2 following preparative SDS-PAGE and electroelution. This data was used to confirm the translation start site for the corresponding gene. The N-terminal five amino acids determined experimentally match residues 2 through 6 predicted from the DNA sequence of the first open reading frame. Translation of this reading frame predicts a polypeptide of 25,000 molecular weight. The translation product of the first open reading frame starting at the ATG, nucleotide 37 and ending at the TGA stop codon nucleotide is shown in FIGS. 6a and 6b. This is the predicted primary amino acid sequence of the AcetoAcetyl-CoA reductase protein.

It is evident that the Acetoacetyl-CoA reductase gene in clones pZT1 and pZT2 can be expressed at reasonably high levels in E. coli. However, in both of these cases, the expression of the reductase gene from the tac promoter is not optimum due to the presence of the thiolase structural gene and 5'-flanking sequence. Since there is a 5.9-fold inhibition of tac directed expression of thiolase promoter and both of these plasmids express the thiolase gene at high levels which could present problems in purification by affinity chromatography, a simpler Acetoacetyl-CoA reductase overproduction vector, pZR14, shown in FIG. 2, was constructed. pUCDBK1 DNA was digested to completion with SalI and SmaI and the SalI ends repaired using the Klenow fragment of DNA polymerase. Following the addition of EcoR1 linkers and digestion with EcoR1, the fragments were separated by agarose gel electrophoresis. The 1.05 kb fragment corresponding to the Acetoacetyl-CoA reductase structural gene plus 36 bp flanking the 5'-end and 266 bp flanking the 3' end was purified and ligated into the EcoR1 site of pKK223-3. pZR14 was then identified as having the correct restriction map with the reductase gene in the right orientation. Induction experiments were performed on pZT14 as described for pZT1, pZT2 and pZT3. Acetoacetyl-CoA reductase was expressed.

Identification of the Thiolase and Reductase Genes in A. eutrophus

The methods used in isolating the first two PHB genes from Zoogloea were applied to the identification, isolation and characterization of genes from another PHB producing species, Alcaligenes eutrophus, using the Zoogloea thiolase gene region as a hybridization probe to locate homologous sequences.

Subsequent sequence analysis of a 2 kb PstI fragment of A. eutrophus DNA cloned into pUC8 (clone pAeT3), restriction mapped in FIG. 7 has clearly identified the corresponding thiolase gene region in the A. eutrophus H16 genome. The downstream sequences in pAeT3 are also homologous to the NADP-linked reductase gene region from the Zoogloea clone pUCDBK1. The sequences of the Alcaligenes thiolase and reductase genes is shown in FIG. 8a and 8b.

Cloning of the thiolase and reductase genes from pAeT3 into pKK 223.3, as shown in FIG. 7, leads to expression of the corresponding enzymes. Comparisons of the Zoogloea and A. eutrophus thiolase protein sequences establish that the two proteins have a total of 68% identical residues including the active site Cys-89.

Both the A. eutrophus and Zoogloea thiolase gene regions were used as hybridization probes to screen Nocardia DNA to identify the corresponding Nocardia genes. Techniques for identifying the thiolase, reductase, and other polymerase genes from other species having homologous sequences in addition to those described above, are known to those skilled in the art.

Identification of the Z. ramigera PHB polymerase gene

PHB polymerase from Z. ramigera utilizes D(-)-hydroxybutyryl-CoA monomers, polymerizing them in oxoester linkages in a template-independent head to tail condensation to yield linear polymers. These polymers can contain up to 10,000 monomer units with a molecular weight in excess of $1 \times 10^6$. The polymer rapidly becomes insoluble and accumulates as discrete granules in the cell. Of fundamental interest is the mechanism by which this unique enzyme polymerizes water soluble monomers, transporting them from the cytoplasm into a hydrophobic highly crystalline granule.

Using a conjugal transfer system based on derivatives of the broad host range plasmid pRK290 described by Ditta et al., in *Proc. Natl. Acad. Sci. USA* 77, 7347–7351 (1980), transposon mutagenesis and complementation analysis can be performed in *Z. ramigera*. PHB negative mutants of *Z. ramigera* are isolated, characterized and then complemented. As described by Schlegel et al., *Arch. Microbiol.* 71, 283–294 (1970), sudan-black staining is used for the detection of PHB negative mutants. Complementation of the mutants is screened for by growing, harvesting, and lysing the cells to release PHB that can then be purified to determine its presence and molecular weight size distribution. Thiolase, reductase and PHB polymerase activities in the lysates are also assayed.

When the Sudan black screening technique was applied to *Z. ramigera*, at least two Tn5 sudan black negative (PHB negative) mutants were identified and characterized. Construction of Tn5 mutant libraries is facilitated by using an exopolysaccharide negative strain, *Z. ramigera* S99, described by Easson et al. (1987) submitted to the *Journal of Bacteriology* to overcome the problems of polysaccharide interference with the conjugation process and the screening procedure. Methods for mutating and isolating *Z. ramigera* strains is described in our co-pending application U.S. Ser. No. 035,604, filed Apr. 7, 1987, by Easson et al, entitled "Method to Control and Produce Novel Biopolymers".

A complete library of PHB mutants defective in each step of the pathway has been established. A similar Tn5 mutant library of *A. eutophus* H16 has also been constructed. From the knowledge of the genomic organization of the thiolase and the reductase genes, it is relatively straightforward to screen PHB polymerarse mutants by Southern hybridization analysis using $^{32}$P-labelled Tn5 as a probe to identify the location of this gene. Complementation of the mutants is achieved using the cosmid library described by Easson et al. (1987).

The polymerase complementing sequences are subcloned in a straightforward manner using techniques known to those skilled in the art on a smaller three to five kb restriction fragment for DNA sequencing. Computer analysis, utilizing the codon usage data from thiolase and reductase as the Zoogloea standard can be used to locate the protein coding regions. Sequences 5' to the potential translation start signal, to be confirmed by protein sequence data, are analyzed for regulatory sequences and then the transcription initiation site determined by S1-nuclease mapping.

Modification of Polymer Synthesis by Varying Levels of Enzyme Expression

After isolation and characterization of the polymer genes and gene products from a variety of organisms, as demonstrated for *Z. ramigera, A. eutrophus*, and *N. salmonicolor*, means for controlling the expression of the gene products are established. Overproduction of the Zoogloea thiolase gene was demonstrated by the studies used to define the transcription start site and promoter of the *Z. ramigera*. Overproduction enables the purification of the enzymes to homogeneity and provides reagent type quantities for analysis and comparison of substrate specificieties. In addition, the purified enzymes can be used to synthesize stereospecific substrates for in vitro polymer synthesis. Further, once the transcriptional regulatory mechanism responsible for polymer over-production is elucidated under a variety of environmental conditions, in vitro systems for the enzymatic synthesis of known polymers, and novel polymers, can be developed to provide new materials. The new materials are then analyzed for chemical composition, molecular weight and rheological characteristics so that maximum utilization can be made of the polymers.

An overproduction system for the *Z. ramigera* thiolase in *E. coli* was constructed using the synthetic tac promoter to produce a series of thiolase expression plasmids, the optimum construct in induced *E. coli* cells yielding about 20–30% of the total soluble cell protein as thiolase. This method yields thiolase in reagent type quantities, an average of 150 mg pure thiolase from 1 liter of culture. There are essentially two conditions where gene regulation in *Z. ramigera* and *A. eutrophus* may be expected to occur: when carbon starved cells under nutrient limiting conditions are subsequently presented with a carbon source and when cells grown under nutrient limiting conditions have accumulated large amounts of PHB and the carbon source in the medium becomes depleted resulting in PHB degradation.

Transcriptional regulation of the polymer biosynthetic genes is determined as follows. Cultures grown under various conditions are harvested both for enzyme assays (thiolase, reductase and polymerase) and for RNA purification. RNA samples are analyzed in a series of Northern hybridization experiments using the cloned genes as probes. Useful RNA hybridization methodology includes glyoxylation of RNA (McMaster and Carmichael, *Proc. Natl. Acad. Sci. USA* 74, 4835 (1977)); formaldehyde/agarose gel electrophoresis (Lehrach et al., *Proc. Natl. Acad. Sci. USA* 16, 4743 (1977)); transfer to nitrocellulose or nylon filters (Thomas, *Proc. Natl. Acad. Sci. USA* 77, 5201 (1980)); and hybridization with DNA probes labelled with $^{32}$P by nick translation (Rigby et al., *J. Mol. Biol.* 113, 237 (1977)). Probes are prepared from clones pUCDBK1(*Z. ramigera*); and pAeT3 (*A. eutrophus*). One result of these studies is the establishment of the operon organization of the genes and the length of the mRNA.

The levels of each of the biosynthetic enzymes are manipulated and the effect this has on polymer synthesis monitored. It is necessary to determine the rate-limiting enzyme(s) in the biosynthetic pathway so that one can increase flux through the pathway by overproducing the rate-limiting enzyme; the effect overproduction of each enzyme has on the incorporation of different monomeric units, i.e., the ratio of PHB:PHV in the copolymer produced by *A. eutrophus* when grown on butyrate; and the result of expression of the genes from one species in other species, for example, the expression of Zoogloea genes in *A. eutrophus*, and vice versa, as well as other isolated and characterized heterologous genes from other organisms, e.g., Nocardia and *P. oleovarans* in Zoogloea and *A. eutrophus*.

To accomplish overproduction of polymer biosynthetic genes in multiple host organisms, one must use broad host range cloning vectors which function in these bacteria. In one instance, enzyme overproduction via gene dosage is carried out. For example, the entire pUCDBK1 insert containing the promoter region can be cloned into the vector pSUP104 (Simon et al., *Molecular Genetics of the Bacteria-Plant Interaction*, A. Pobler, ed. (Spring-Verlag, N.Y. 1983) and used to transform *Z. ramiger* I-16-M. The extent of overproduction of each enzyme is monitored by enzyme assays. A similar approach can be taken for any number of other genes; for example, thiolase; thiolase and reductase; reductase; reductase and polymerase, etc. Secondly, genes can be placed under the transcriptional control of high efficiency promoters, i.e., tac (Gill et al., *J. Bact.* 167, 611–615 (1986) and tol (Mermod et al., *J. Bact.* 167, 447–454 (1986). In this case, the constructs are conjugated into mutants defective in the corresponding gene. The expression of the polymer biosynthetic gene or genes of interest can then be tightly regulated, as determined using enzyme assays to monitor the level of overproduction. As each construct is tested, one can begin to monitor the effect on polymer synthesis in a routine manner i.e., the rate and level of synthesis.

Modification of Polymer Synthesis by Altering Available Substrate or Enzyme Specificity Factors which determine the molecular weight of the PHB produced by different bacteria can be elucidated by analysing the molecular weight distribution of the polymers produced by various bacteria. There is little doubt that a number of PHB-producing microorganisms have the ability to incorporate monomers other than D(-)-hydroxybutyrate into the polymer chain. For the PHB-PHV copolymer produced by A. eutrophus, it has been proposed that propionate is first converted to propionyl-CoA which then acts as a substrate for beta-ketothiolase. The high yields of pure enzymes available from over-production systems is necessary to determine the range of alternate substrates which each of the three PHB-biosynthetic enzymes can utilize and the types of new PHB-like polymers that can be synthesized in an in vitro system where the available substrates can be strictly controlled.

Although the thiolase and reductase enzymes are an essential part of the biosynthesis of PHB and PHB-like polymers, it is the PHB polymerase which ultimately defines the new types of polymer which can be made. This is facilitated by the development of an in vitro system using the enzyme to test a whole range of substrates, many which cannot enter the cell and therefore cannot be tested for incorporation into PHB in a fermentation process.

Overproduction and purification of more than one reductase enzyme provides a means for comparing the kinetics and specificity of the enzymes. The Zoogloea reductase has been reported to be NADP-specific, however, the A. eutrophus enzyme apparently will use either NAD or NADP. The stereospecificity of this enzyme may make it a useful reagent for the synthesis of D-substrates for PHB synthetase studies. Among the acetoacetyl derivatives to be tested are the oxoester of CoA and oxopantetheine pivaloate (OPP) and the methylene analogs. The ketone but not the oxoester of the methylene analogs is cleaved by Zoologea thiolase. Various longer chain alkyl derivatives where R does not equal H, and in particular the $C_5$–$C_8$ linear 3-oxo thiolesters, oxoesters and methylene ketones, may also be useful as substrates for the PHB synthetase, given the existence of $C_5$–$C_8$-beta-hydroxyalkanoates in B. megaterium. We will also examine olefins, alcohols and epoxides.

In crude extracts of Z. ramigera, D-beta-hydroxybutyryl CoA, but not L-hydroxybutyryl CoA, is a substrate for PHB synthetase. It is expected that other D-hydroxyacyl CoA species will utilize alternate substrates or cosubstrates such as D-beta-hydroxyvaleryl CoA (HV-CoA). [2-3H]HB-CoA and beta [3-$^{14}$C]-HV-CoA, each readily preparable by enzymic or chemical synthesis, can be used as substrates and to monitor $^3$H and $^{14}$C content and ratios in polymers precipitated or separated by gel filtration. It is predicted that block copolymer regions, e.g., $(HB)_{500}(HV)_{1000}(HB)_{500}$, can be constructed by careful control of substrate ratios, and leaving groups in elongation phase, e.g., HB-oxo-CoA and HV-S-CoA monomers.

Additional alternate substrates can be tested including branched chain beta-hydroxyacyl CoAs. Testing cannot be done in whole cells since such compounds are not normally transported. Alternate substrates will be tested for inhibition of normal [$^{14}$C]-PHB formation first by incorporation of soluble [$^{14}$C]-HBCoA into insoluble polymer, then as copolymerization cosubstrates and finally for homopolymerization. Alternate substrates will be assayed for $K_m$, $V_{max}$ relative to HB-CoA and for polymer size determined by calibrated gel filtration studies.

FIG. 9 summarizes some of the monomeric acyl CoA analogs of D-3-hydroxybutyryl-CoA to be tested as substrates for PHB polymerase and also diagrams a proposed repeating unit that would arise from homopolymeric polyester formation or of a block region in a block copolymer from enzymatic co-incubation with HB-CoA to yield PHB formation itself. Entry 2 is the isomeric 2-hydroxybutyryl CoA and would yield a diagnostic ethyl signal by NMR and a 1,2-ester link rather than a 1,3 link. This would alter polymer properties even at a low mole percent incorporation. Entry 3 is the 4-hydroxybutyryl CoA isomer and would yield a longer 1,4-ester link, possibly more crystalline. Entry 4 is known from in vivo work to be a substrate for copolymerization with entry 1. It may actually serve as a substrate for homopolyester production with either Zoogloea or Alcaligenes pure PHB synthase. Entry 5 is the corresponding 2—OH $C_5$substrate and yields both 1,2-1inkage and propyl branching, detectable by proton and $^{13}$C NMR.

Entries 6 and 7 introduce $C_4$ and $C_5$ vinyl branched units in 1,2 and 1,3-ester linkages (detectable by IR) and entry 8 introduces an epoxy-functionalized polyester. These three products can be subjected to radical-initiated cross-linking to covalently attach adjacent polyester chains by cross-linking. Lastly, entries 9 and 10 probe steric requirements at $C_3$ and $C_2$ for PHB synthase. They yield homopolymers or regions of copolymer even less crystalline than poly HB/HV, which is a better performing thermoplastic material than PHB.

Substrates listed in FIG. 9 are representative acyl thiolester candidates for PHB synthetases. They are straightforward to prepare and easily assayed. Promising results can be followed by $^{14}$C or $^{13}$C-enrichment for more quantitative analysis of mole fraction incorporated into polyester product. It is extremely likely that a number of these analogs will be polymerized. The initial rates (assayable by $^{14}$C-incorporation or by dithiobisnitrobenzoate-titratable CoASH release), size of product (gel filtration, radioactivity analysis) and material properties can then be evaluated.

Physical and Chemical Analysis of PHB and PHB-like Biopolymers

For chemical and physical properties analysis, the materials are first purified from fermentation processes or from enzymatic reactions. In the case of whole cells, the biopolymer is extracted by the sodium hypochlorite method. Polymers synthesized in vitro are extracted with chloroform.

Purification of PHB Granules

Concurrent with the molecular studies, large quantities of PHB granules from Z. ramigera are purified according to the method of Fukui et al, Arch. Microbiol. 110, 149-156 (1976). This procedure results in yields of over 10 gram of PHB per liter cells. Protein containing PHB polymerase activity, which accounts for between 1 and 2% of the granules, is extracted by mild alkali treatment as described by Griebel and Merrick, J. Bacteriol. 108, 782–789 (1971). Analysis of the protein by SDS-polyacrylamide gel electrophoresis is of use in identifying the size and number of polypeptides associated with the PHB granules. Preparative SDS-PAGE and electroelution of protein bands is used to provide material for $NH_2$-terminal sequence analysis, thereby permitting the design of oligonucleotides and the preparation of antibodies for immunological screening, as described for the thiolase.

In an example of the purification of overproduced thiolase, plasmid containing *E. coli* JM105 cells were grown in 2×TY medium containing 50 microgram/ml ampicillin. One liter of cells was grown to an $A_{595}$ of 0.6–0.7 and induced by the addition of IPTG to a final concentration of 2 mM. Inductions were performed for 16 h and the cells harvested by centrifugation. All remaining procedures were carried out at 4° C. with pre-cooled solutions. Cell pellets were resuspended in 30 ml of lysis buffer (20 mM Tris HC1, pH 8.0; 5 mM EDTA; 5 mMbeta-mercaptoethanol; 0.02 mM phenylmethylsulfonyl fluoride; 5% (v/v) glycerol) and lysed by sonication. Cell debris was subsequently removed by centrifugation.

DEAE CL6B Sepharose (Pharmacia Fine Chemicals, Piscataway, N.J.) was activated as per manufacturers instructions and pre-equilibrated with lysis buffer. Two methods were used for this step. A batch procedure was carried out by mixing one-half of the lysate supernatant with 25 ml of packed DEAE CL6B Sepharose resin for 10 min to bind the protein. After binding, the resin was washed with 2×25 ml lysis buffer and 2×25 ml lysis buffer containing 75 mM KCl. Thiolase containing protein was subsequently eluted with 3×25 ml lysis buffer containing 0.2 M KCl, with incubations for 30 min, 1 h and 12 h. Alternatively, a DEAE CL6B column (2.5 cm×25 cm) was set up and eluted with a linear 0 to 1M KCl gradient (300 ml of each in lysis buffer).

Reactive Red 120-agarose type 3000-CL (Sigma, St. Louis, Mo.) was activated with 1 column volume (2.5 cm×35 cm) of 7M urea in 0.5M NaOH and equilibrated with lysis buffer containing 0.2M KCl. Eluant from the DEAE step was loaded directly onto the Red gel column without prior treatment and washed with 2 column volumes of 0.2M KCl in lysis buffer. Protein was eluted with a linear 0.2–2M KCl (30 ml each) gradient in lysis buffer. Fractions containing thiolase were pooled and dialyzed against 4 liters of 10 mM Tris HC1, pH 7.5; 5 mM beta-mercaptoethanol; 1 mM EDTA. Purified protein was stored at 4° C. in dialysis buffer containing 50% w/v) glycerol.

Purification of the native PHB polymerase from granules has not been very successful. In contrast, the soluble enzyme can be purified 50-fold to a specific activity of 1.1 mole substrate polymerized/min/mg via DEAE Sepharose and hydroxyapatite chromatography. A strategy of chromatography on DEAE followed by affinity chromatography on various ligand-substituted Sepharoses, such as oligohydroxybutyryl Sepharose, Octyl Sepharose 4B, and butyl toyopease (Toyo Soda Co.) can be employed to purify the overproduced enzyme, using methods known to those skilled in the art.

The following assays and parameters must be determined to fully characterize the purified polymers: chemical analysis; molecular weight distribution: hydrodoynamic volume; viscosity; chain conformations; chain interactions; and time functions.

Subunit composition is assayed by a method involving treatment of the polyesters with ethanolic HCl, followed by GC analysis of the hydroxyacyl ethyl esters. Where appropriate, fractions are monitored for radioactivity. The detection limit is 100 femtamoles ($10^{-12}$ moles) and routine analysis has been reported on 100 nanograms of polymer (Findlay and White, *Appl. Environ. Micro.* 45, 71–78, 1983). PHB and related polymers have relatively simple repeating units compared with the more usual biopolymers such as proteins or polysaccharides. The repeating units of 4 or 5 carbon atoms can be established by $^1$H and $^{13}$C NMR, by analyzing the number and relative positions. of NMR signals, in combination with the proton-proton and carbon-proton coupling patterns. The repeating units, 4 or 5 carbons, are indicated by the $^{13}$C NMR spectra. Homopolymer structure can be confirmed with NMR analysis. For heteropolymers, the relative content of the different monomers can be evaluated by their relative intensitites in the NMR spectrum. For example, the relative areas of the two methyl groups at σ=0.85 and σ=1.21 can be used to determine the relative content of the two monomers in bacterial poly beta-hydroxybutyrate co-beta-hydroxypentanoate (Capon et al., *Phyto Chemistry* 22, 1181–1184 (1983); Bloemberge et al., *Am. Chem. Soc. Div. Polym. Chem.* 27, 252 (1986)). Monomer sequence can also be determined in some cases by NMR analysis (Grasdalen et al., *Carbohydrate Res.* 68, 23–31 (1979); Iida et al., *Macromolcules* 11, 490–493 (1978)).

The molecular weight distribution of PHB polymers is determined by calibrated gel filtration studies (Barham et al., *J. Materials Sci.* 19, 2781–2794 (1984); Suzuki et al., *Appl. Microbiol. Biotechnol.* 23, 322–329 (1986)). The gel permeation mobilities have been related to absolute molecular weights using molecular weight-dependent intrinsic viscosity by Mark-Houwink-Sakurada parameters. Columns are microstyragel, run in $CHCl_3$ at 30° C., analyzed with I.R. detector and calibrated with polystyrene (Barham et al., (1984)).

The hydrodynamic volume of individual molecules of PHB can be evaluated from the intrinsic viscosity determined from dilute solutions of PHB. The viscosity of suspensions of particles are described in terms of the difference between the macroscopic viscosity n' of the suspension and the viscosity n of the pure solvent. Specific viscosity, $n_{sp} \equiv (n'-n)/n$. The specific viscosity, in the limit of infinite dilution, should be proportional to the number of suspended particles per unit volume. In a macromolecular solution, $n_{sp}$ is proportional to the concentration, C, in grams per cubic centimeter. Thus $n_{sp}/C$, reduced viscosity, should be independent of concentration, as it is the limit of zero concentration. This limiting value of $n_{sp}/C$ gives intrinsic viscosity [n], $$[n] = \lim_{c \to 0} \frac{n_{sp}}{c} = \lim_{c \to 0} \frac{n'-n}{nC}$$

The intrinsic viscosity can be determined by measuring (n'−n)/nC at various concentration and extrapolating to C=0. Alternatively, the intrinsic viscosity can be obtained by measuring (1/C)ln(n'/n) and extrapolating to zero concentration. For, ln(n'/n)=[1+(n'/n)/n]. As the limit of zero concentration is approached, (n'/n)/n becomes very small, and the logarithm may be replaced by (n'−n)/n; i.e., $$\lim_{c \to 0} \frac{1}{C} \ln \frac{n'}{n} = \lim_{c \to 0} \frac{n'-n}{nC}$$

The viscosity of dilute solutions of PHB are measured using a Fenske-Cannon type capillary viscometer. The time, t, for a given volume of liquid, V, as defined by the two etched lines in the Viscometer, to flow through the capillary of length, L, and radius, r, is measured. If the density of the liquid, p, is known, the viscosity can be calculated from the Poiseuille equation:

$$n = \frac{\pi r^4 tP}{8LV}$$

where n is the absolute viscosity and P, the applied pressure differential is defined by P=hgp, where h is the average height of the liquid in the tube and g is the acceleration due to gravity. In practice, the flow time for a liquid of known viscosity is measured and a viscometer constant, A, is determined such that the kinematic viscosity (Y=n/p) and A are defined by the equations:

$$y = At \text{ and where } A = \frac{h' r^4 g}{8LV}$$

Chain conformation of PHB and related polymers are estimated by the molecular weight dependency of intrinsic viscosity as indicated by the Mark-Houwink constant, a, as follows:

$$[n]=K(MW)^a$$

The Mark-Houwink constant indicates the progression of polymer backbone as the molecular weight increases and therefore can describe the overall chain conformation. A Mark-Houwink constant close to zero indicates rigid spherical shape conformation, between 0.5 and 0.7 indicates equivalent sphere random coil, 0.7 and 1.0 indicates free draining random coil and 1.2 or above indicates rigid-rod conformation. Such information is critical for applications and fabrication procedures for such molecules. Polymer produced under various conditions (i.e., fermentation time) or polymer subjected to sonication or enzymatic degradation will be used to determine the intrinsic viscosity at a wide range of molecular weights. The Mark-Houwink constants for PHB and related polymers are also a function of the test solvent and therefore intrinsic viscosity measurements must be made over several molecular weight values.

Polymer-polymer interactions are evaluated by steady shear viscosity determined for various concentrations of a given biopolymer. The steady shear viscosity-concentration with C[n]curve, as high as the solubility permits, is constructed to evaluate intermolecular chain interactions. The ratio of the concentration at which viscosity concentration deviates from linearity and the reciprocal of the intrinsic viscosity will be used to represent interchain interactions.

Polymer-polymer chain interactions are evaluated by the viscoeleastic behavior. The storage and loss modules can be determined in the frequency range of $10^{-3}$ to 10 Hz using a Bohlin Rheometer System (Lund, Sweden). Assuming that the rubber elasticity holds in the rubbery region, the length of chain segment between the crosslinks, $N_c$, is estimated according to Florey, *Principles of Polymer Chemistry*, Chapter 11, pages 432–494 (Cornell Univ. Press, Ithaca, N.Y., 1953) using the elastic modulus (G') from rubbery regions where G' is independent of frequency. The frequency at which elastic modulus (G') equals loss modulus (G') for various concentration of polymers should be evaluated also to indicate degree of chain interations.

$$M_c = \frac{CRT}{G'}$$

The viscosity of polymers as a function of shear ratio (0.01 to 300 $sec^{-1}$) is determined at 25° C. using a Bohlin Rheometer System (Lund, Sweden). The lower Newtonian, pseudoplastic and higher Newtonian region should be determined. Characteristic time is estimated from the reciprocal of the shear rate at which lower Newtonian region ends. The hysteresis effect is determined by subjecting polymer solutions to repeated shear cycles. The relaxation time is determined directly using the Bohlin Rheometer.

Modifications and variations of the present invention, a method for making polyhydroxybutyrate and polyhydroxybutyrate-like polymers having carbon-carbon backbones using recombinant engineering according to the foregoing detailed description, and the resulting polymers, will be obvious to those skilled in the art. Such variations and modifications are intended to come within the scope of the appended claims.

We claim:

1. An isolated DNA sequence hybridizing to a gene encoding beta-ketothiolase when incubated for a period of approximately 16 to 18 hours at a temperature of 65° C. in a mixture of a 5x solution of 0.15M NaCl, 0.15M sodium citrate, 20 mM sodium phosphate, 5x Derthardt's solution, 0.1% (w/v) SDS, 10 mM EDTA, and 100 µg/ml sonicated denatured salmon DNA.

2. The DNA sequence of claim 1 which hybridizes to the gene shown in FIG. 3 or 8 when incubated for a period of approximately 16 to 18 hours at a temperature of 65° C. in a mixture of a 5x solution of 0.15 M NaCl, 0.15M sodium citrate, 20 mM sodium phosphate, 5x Denhardt's solution, 0.1% (w/v) SDS, 10 mM EDTA, and 100 µg/ml sonicated denatured salmon DNA.

3. The DNA sequence of claim 2 having the sequence shown in FIG. 3 or conservative substitutions thereof.

4. The DNA sequence of claim 2 having the sequence shown in FIG. 8 or conservative substitutions thereof.

5. An organism genetically engineered to express the gene of claim 1 encoding beta-ketothiolase which occurs naturally and is expressed in a bacteria selected from the group consisting of Zoogloea, Bacillus, Nocardia, Clostridium, Halobacterium, Pseudomonas, and Alcaligenes.

* * * * *